US009919280B2

(12) United States Patent
Schlenoff et al.

(10) Patent No.: US 9,919,280 B2
(45) Date of Patent: Mar. 20, 2018

(54) METHOD OF FORMING POLYELECTROLYTE COMPLEX CAPSULES

(71) Applicant: The Florida State University Research Foundation, Inc., Tallahassee, FL (US)

(72) Inventors: Joseph Schlenoff, Tallahassee, FL (US); Qifeng Wang, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 332 days.

(21) Appl. No.: 14/930,784

(22) Filed: Nov. 3, 2015

(65) Prior Publication Data

US 2016/0144328 A1 May 26, 2016

Related U.S. Application Data

(60) Provisional application No. 62/083,583, filed on Nov. 24, 2014.

(51) Int. Cl.
*A61K 9/50* (2006.01)
*B01J 13/04* (2006.01)
*B01J 13/10* (2006.01)

(52) U.S. Cl.
CPC ............... *B01J 13/04* (2013.01); *B01J 13/10* (2013.01); *A61K 9/5026* (2013.01)

(58) Field of Classification Search
None
See application file for complete search history.

(56) References Cited

U.S. PATENT DOCUMENTS

| | | | | |
|---|---|---|---|---|
| 3,276,598 | A | 10/1966 | Michaels et al. | |
| 3,546,142 | A | 12/1970 | Michaels et al. | |
| 3,558,744 | A | 1/1971 | Michaels et al. | |
| 3,565,973 | A | 2/1971 | Michaels | |
| 4,539,373 | A | 9/1985 | Mani et al. | |
| 5,260,002 | A * | 11/1993 | Wang | A61K 9/1694 264/11 |
| 5,418,154 | A * | 5/1995 | Aebischer | A61F 2/022 264/4 |
| 6,001,312 | A * | 12/1999 | Wang | B01J 13/04 264/4.33 |
| 6,660,367 | B1 | 12/2003 | Yang et al. | |
| 6,905,875 | B2 | 6/2005 | Yu et al. | |
| 7,101,947 | B2 | 9/2006 | Schlenoff et al. | |
| 7,105,229 | B2 | 9/2006 | Anderson | |
| 7,223,327 | B2 | 5/2007 | Schlenoff et al. | |
| 7,238,536 | B1 | 7/2007 | Schlenoff | |
| 7,387,824 | B2 | 6/2008 | Tamagawa et al. | |
| 2003/0230819 | A1* | 12/2003 | Park | A61L 31/16 264/4 |
| 2004/0265603 | A1 | 12/2004 | Schlenoff | |
| 2005/0026801 | A1* | 2/2005 | Broeckx | B01J 13/02 510/276 |
| 2005/0176620 | A1 | 8/2005 | Prestwich et al. | |
| 2005/0282925 | A1 | 12/2005 | Schlenoff et al. | |
| 2005/0287111 | A1 | 12/2005 | Schlenoff et al. | |
| 2006/0051532 | A1 | 3/2006 | Tamagawa et al. | |
| 2006/0065529 | A1 | 3/2006 | Schlenoff et al. | |
| 2006/0073333 | A1 | 4/2006 | Anderson | |
| 2007/0259452 | A1 | 11/2007 | Schlenoff | |
| 2007/0265174 | A1 | 11/2007 | Schlenoff | |
| 2014/0011033 | A1* | 1/2014 | Carreras | A61K 9/1652 428/402.21 |
| 2015/0250689 | A1* | 9/2015 | Dardelle | B01J 13/10 510/130 |
| 2016/0332131 | A1* | 11/2016 | Lee | B01J 13/10 |

OTHER PUBLICATIONS

Allen, Norman S., "Polymer Photochemistry", Photochemistry, 2007, vol. 36, pp. 232-297.
Biggerstaff et al., "Damping Performance of Cocured Graphite/Epoxy Composite Laminates with Embedded Damping Materials", Journal of Composite Materials, 1999, vol. 33, No. 15, pp. 1457-1469.
Dai et al., "Controlling the Permeability of Multilayered Polyelectrolyte Films through Derivatization, Cross-Linking, and Hydrolysis", Langmuir, 2001, vol. 17, No. 3, pp. 931-937.
Dubas et al., "Swelling and Smoothing of Polyelectrolyte Multilayers by Salt", Langmuir, 2001, vol. 17,pp. 7725-7727.
Graul et al., "Capillaries Modified by Polyelectrolyte Multilayers for Electrophoretic Separations", Analytical Chemistry, 1999, vol. 71, No. 18, pp. 4007-4013.
Holmlin et al., "Zwitterionic SAMs that Resist Nonspecific Adsorption of Protein from Aqueous Buffer", Langmuir, 2001, vol. 17, No. 9, pp. 2841-2850.
Iatridis et al., "The Viscoelastic Behavior of the Non-Degenerate Human Lumbar Nucleus Pulposus in Shear," J. Biomechanics, 1997, vol. 30, No. 10, pp. 1005-1013.
Iatridis et al., "Shear Mechanical Properties of Human Lumbar Annulus Fibrosus", Journal of Orthopaedic Research, 1999, vol. 17, No. 5, pp. 732-737.
Jaber et al., "Mechanical Properties of Reversibly Cross-Linked Ultrathin Polyelectrolyte Complexes", Journal of American Chemical Society, 2006, vol. 128, pp. 2940-2947.
Kozlovskaya et al., "Hydrogen-Bonded Polymer Capsules Formed by Layer-by-Layer Self-Assembly", Macromolecules, 2003, vol. 36, pp. 8590-8592.
Lim et al., "Microencapsulated Islets as Bioartificial Endocrine Pancreas", Science, New Series, 1980, vol. 210, No. 4472, pp. 908-910.

(Continued)

*Primary Examiner* — Mary Lynn F Theisen
(74) *Attorney, Agent, or Firm* — Armstrong Teasdale LLP

(57) ABSTRACT

Polyelectrolyte complex microcapsules are prepared by a novel template- and surfactant-free method. The microcapsules are produced spontaneously by ultrasonically spraying a solution of complex into a hot water reservoir which enhances diffusion and relaxation of polymer. The size and wall thickness of microcapsules are precisely controlled. Encapsulation of polymers and nanoparticles by mixing them with polyelectrolyte solutions is demonstrated.

35 Claims, 7 Drawing Sheets

(56) References Cited

OTHER PUBLICATIONS

Losche et al., "Detailed Structure of Molecularly Thin Polyelectrolyte Multilayer Films on Solid Substrates as Revealed by Neutron Reflectometry", Macromolecules, 1998, vol. 31, No. 25, pp. 8893-8906.
Michaels, Alan S., "Polyelectrolyte Complexes", Industrial & Engineering Chemistry, 1965, vol. 57, No. 10, pp. 32-40.
Rosidian et al., "Ionic Self-Assembly of Ultrahard ZrO2/Polymer Nanocomposite Thin Films", Advanced Materials, 1998, vol. 10, No. 14, pp. 1087-1091.
Smets, G., "Photocross-Linkable Polymers", Journal of Macromolecular Science Chemistry, 1984, A21(13 & 14), pp. 1695-1703.
Strehmel, Veronika, "Epoxies: Structures, Photoinduced Cross-Linking, Network Properties, and Applications", Handbook of Photochemistry and Photobiology, 2003, Chapter 1, pp. 1-110.
Sui et al., "Phase Separations in pH-Responsive Polyelectrolyte Multilayers: Charge Extrusion versus Charge Expulsion", Langmuir, 2004, vol. 20, No. 14, pp. 6026-6031.
Timpe, Hans-Joachim, "Polymer Photochemistry and Photo-Cross-Linking", Desk Reference of Functional Polymers: Syntheses and Applications, 1997, pp. 273-291.
Poly(Ethylene Glycol) Chemistry: Biotechnical and Biomedical Applications (Table of Contents only), Edited by Milton J. Harris, 1992, Plenum Press, New York, New York, 13 pages.
R. Reese Handbook of Antibiotics (Table of Contents and Preface only), Third Edition, 2000, 3 pages, Lippincott Williams and Wilkins, Philadelphia, Pennsylvania.
International Search Report, PCT/US2007/77146, dated Mar. 7, 2008, 2 pages.
Written Opinion of the International Searching Authority, PCT/US2007/77146, dated Mar. 7, 2008, 8 pages.

* cited by examiner

METHOD OF FORMING POLYELECTROLYTE COMPLEX CAPSULES

CROSS REFERENCE TO RELATED APPLICATION(S)

This application claims the benefit of U.S. Provisional Application Ser. No. 62/083,583, filed Nov. 24, 2014 and titled METHOD OF FORMING POLYELECTROLYTE COMPLEX CAPSULES. The priority provisional application is incorporated by reference herein as if set forth in its entirety.

STATEMENT REGARDING FEDERALLY SPONSORED RESEARCH OR DEVELOPMENT

This invention was made with Government support under Grant DMR 1207188 awarded by the National Science Foundation. The Government has certain rights in the invention.

FIELD OF THE INVENTION

The present invention relates to a method of making hollow, single- and multi-compartment capsules of polyelectrolyte complex, and more specifically to a method of making hollow, single- and multi-compartment capsules of polyelectrolyte complex by spraying.

BACKGROUND OF THE INVENTION

Polyelectrolyte complexes are interpenetrating complexes of one or more predominantly positive polyelectrolytes and one or more predominantly negative polyelectrolytes. The opposite charges on the polymers form ion pairs between chains, holding the chains together. This ion pairing is a type of physical crosslinking.

Polyelectrolyte complexes may be prepared in a straightforward manner by mixing solutions of positive and negative polyelectrolytes. However, the resulting precipitate is gelatinous and difficult to process. The dried complexes, for example, are generally infusible and therefore cannot be injection molded or reformed into articles under elevated temperatures. U.S. Pat. No. 3,546,142 discloses a method for creating solutions of polyelectrolyte complexes using aggressive ternary solvents which are mixtures of salt, water, and organic solvent. Said solutions of dissolved complexes may be cast into films by evaporating the solvent on horizontal plates. Mani et al. (U.S. Pat. No. 4,539,373) point out that the solid polyelectrolyte complexes "are not thermoplastic, i.e., they are not moldable or extrudable, so they must be handled as solutions." Mani discloses a polyelectrolyte complex comprising nonionic thermoplastic repeat units which can be thermally molded.

U.S. Pat. Nos. 8,114,918; 8,206,822; 8,222,306; 8,283,030; 8,314,158; and 8,372,891, which are incorporated fully by reference, disclose how fully hydrated (i.e., complexes in contact with water) polyelectrolyte complexes may be reformed into shapes without raising the temperature, without the addition of organic solvent, and without the need for dissolution, if they are doped with salt ions to a sufficient extent.

An alternative method for producing ultrathin films (less than about 1 micrometer thick) of polyelectrolyte complex is the multilayering method described by Decher et al. in U.S. Pat. No. 5,208,111, wherein a surface is exposed in an alternating fashion to solutions of positive and negative polyelectrolytes. The resulting films are uniform and conformal, though ultrathin. The process, however, can be unacceptably slow, especially if numerous layers of polyelectrolyte are needed.

The multilayering method may be performed on planar or on curved surfaces. For example, polyelectrolyte multilayers have been deposited on particles as described in U.S. Pat. No. 6,479,146. The resulting thin polyelectrolyte complex completely envelopes the particle. Therefore, as disclosed in U.S. Pat. No. 6,479,146, when the particle is dissolved a hollow capsule with walls comprising polyelectrolyte complex remains.

Capsules are often used to package materials in medicine, pharmacy, sensors, microreaction chambers, and catalysts as described in De Geest et al Chem. Soc. Rev. 36, 636-649 (2007) and Becker et al. Small, 6, 1836-1852 (2010).

The method of preparing capsules comprising polyelectrolyte complex disclosed in U.S. Pat. No. 6,479,146 requires building up said complex layer by layer with consecutive depositions of positive and negative polyelectrolytes. After the polyelectrolyte complex is formed, in whole or in part, the particle at the core must now be dissolved to yield the hollow capsule. Often, the material in the core cannot be transported out of the capsule unless the walls are thin. Loading the capsule post synthesis requires yet another processing step.

The process of multilayering, core dissolution and core loading is a time consuming and repetitive process. A much faster method of preparing hollow polyelectrolyte capsules is needed.

SUMMARY OF THE INVENTION

Among the various aspects of the present invention may be noted a method of forming capsules comprising polyelectrolyte complex. In some embodiments, said method comprising spraying a solution or coacervate of polyelectrolyte complex comprising salt into a receiving bath.

The present invention is therefore directed to a method of forming a capsule. The method comprises spraying a polyelectrolyte solution comprising a dissolved positively charged polyelectrolyte and a dissolved negatively charged polyelectrolyte into a liquid receiving bath, wherein upon impacting the liquid receiving bath, the positively charged polyelectrolyte and a negatively charged polyelectrolyte coalesce into a capsule comprising a wall, and further wherein the wall of the capsule comprises an interpenetrating complex of the positively charged polyelectrolyte and the negatively polyelectrolyte.

The present invention is further directed to a method of forming a capsule. The method comprises spraying a coacervate comprising a positively charged polyelectrolyte and a negatively charged polyelectrolyte into a liquid receiving bath, wherein upon impacting the liquid receiving bath, the positively charged polyelectrolyte and a negatively charged polyelectrolyte coalesce into a capsule comprising a wall, and further wherein the capsule wall comprises an interpenetrating complex of the positively charged polyelectrolyte and the negatively polyelectrolyte.

Other objects and features will be in part apparent and in part pointed out hereinafter.

$NaClO_3$ (▲); NaCl (■); $NaNO_3$ (♦) NaBr (○); NaI (♦); $NaClO_4$ (x); and NaSCN (□). Room temperature.

Figure 2:
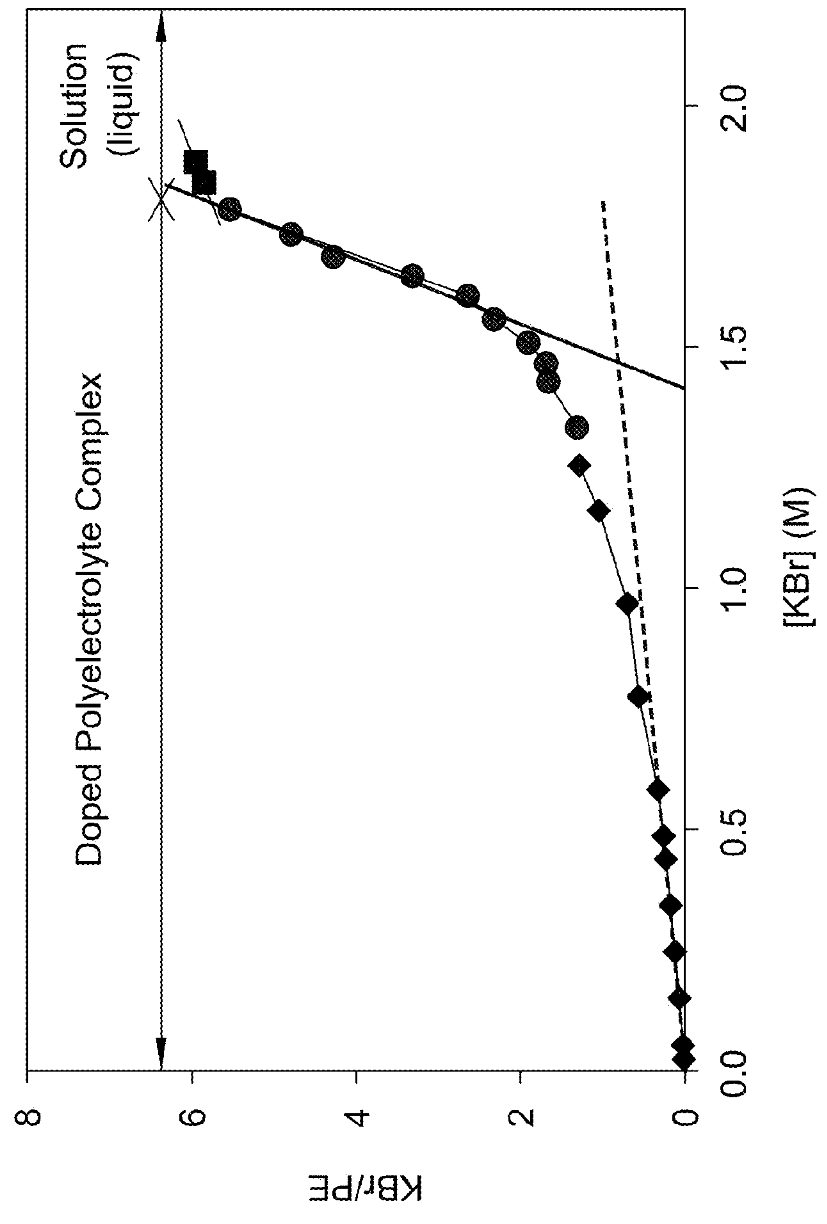

FIG. 2 is graph depicting Molar ratio of KBr to PSS/PDADMA polyelectrolyte complex in doped complex to 1.90M KBr at room temperature. At about 1.8M KBr (■) the doping level reaches 1.00 and beyond this concentration of KBr the complex is dissolved and the polyelectrolyte molecules no longer associate with each other via ion pairing. Dotted line shows doping level, γ, as a function of KBr concentration. When [KBr] reaches about 1.8M the doping level reaches 1.00.

Figure 3:
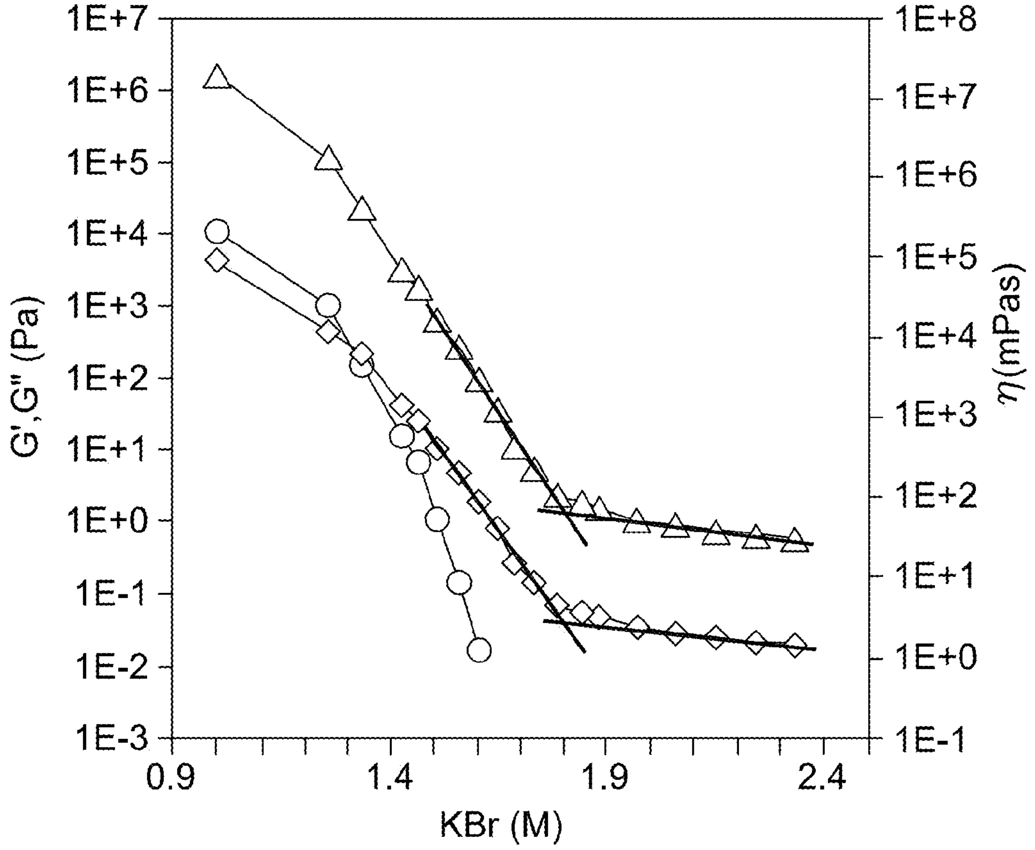

FIG. 3 is a graph depicting dynamic modulus G' (○), G" (◇) and η (Δ) at frequency of 0.1 Hz, shear stress of 25 Pa. 1 centipoise, cP=1 milliPascal second, mPas.

Figure 4A:
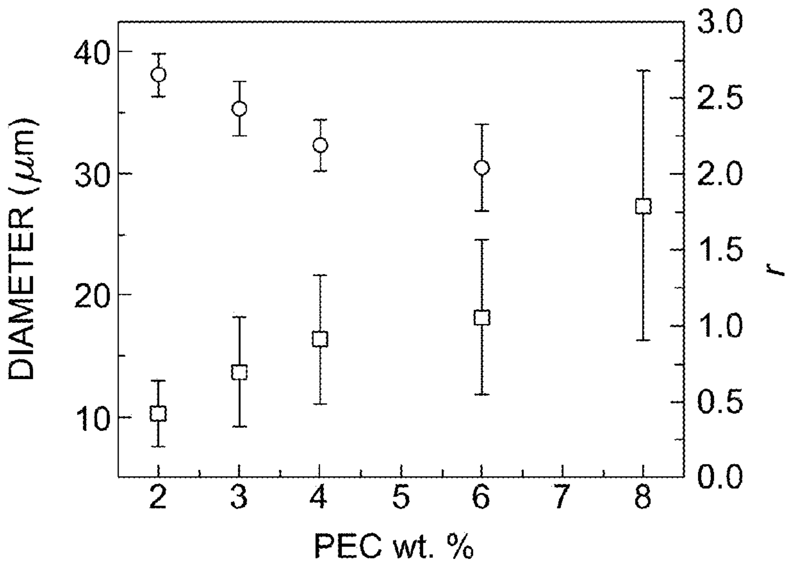

FIG. 4A depicts average diameters (□) and relaxation ratios r (○) vs. the PEC wt. % (a).

Figure 4B:
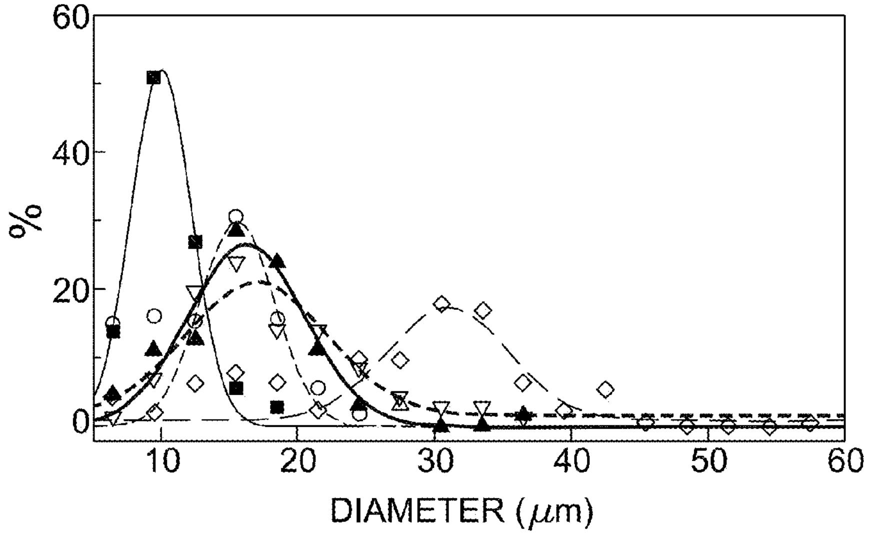
Figure 4C:
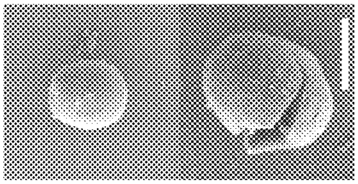
Figure 4D:
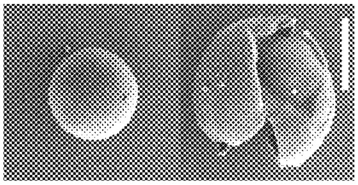
Figure 4E:
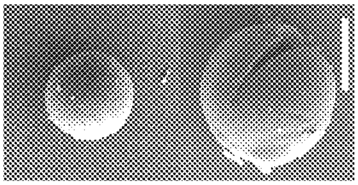
Figure 4F:
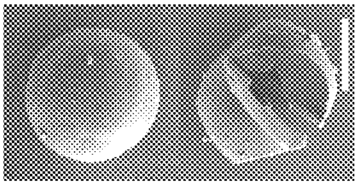

FIG. 4B depicts size distribution of capsules prepared with 2% by weight PEC (■), 3% by weight PEC (○), 4% by weight PEC (▲), 6% by weight PEC (▼) and 8% by weight PEC (◇).

Figure 4G:
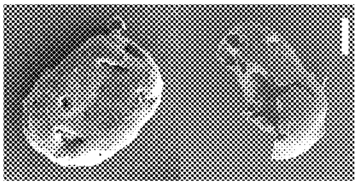
Figure 4H:
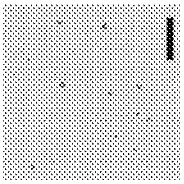
Figure 4I:
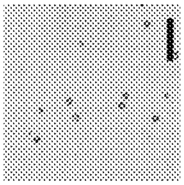
Figure 4J:
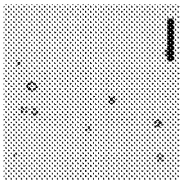
Figure 4K:
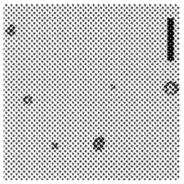

FIGS. 4C, 4D, 4E, 4F, and 4G are SEM images of PEC capsules prepared according to the method of the present invention. The capsules are prepared with 2% by weight PEC (FIG. 4C), 3% by weight PEC (FIG. 4D), 4% by weight PEC (FIG. 4E), 6% by weight PEC (FIG. 4F) and 8% by weight PEC (FIG. 4G). FIGS. 4C through 4G depict the capsules as-prepared and as partially-crushed.)

Figure 4L:
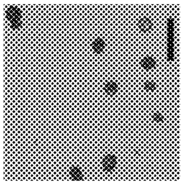

FIGS. 4H, 4I, 4J, 4K, and 4L microscopic images of PEC capsules prepared with 2% by weight PEC (FIG. 4H), 3% by weight PEC (FIG. 4I), 4% by weight PEC (FIG. 4J), 6% by weight PEC (FIG. 4K) and 8% by weight PEC (FIG. 4L). The scale bars are 10 μm (white) and 100 μm (black).

Figure 5A:
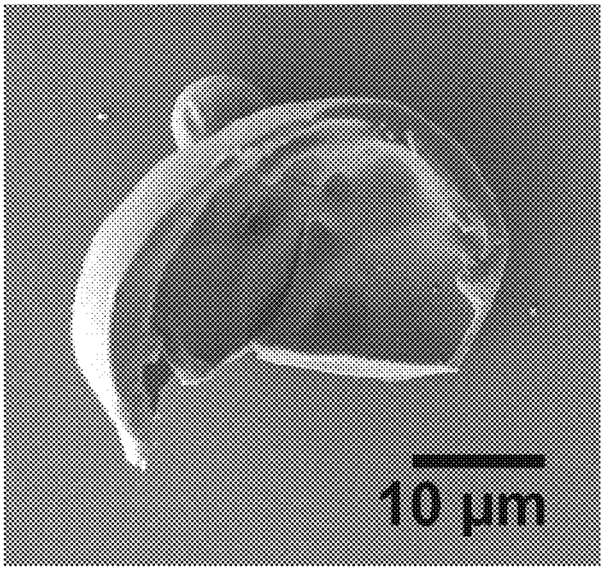

FIG. 5A is an SEM image of a broken PEC capsule. This sample was prepared with 4% by weight PEC solution.

Figure 5B:
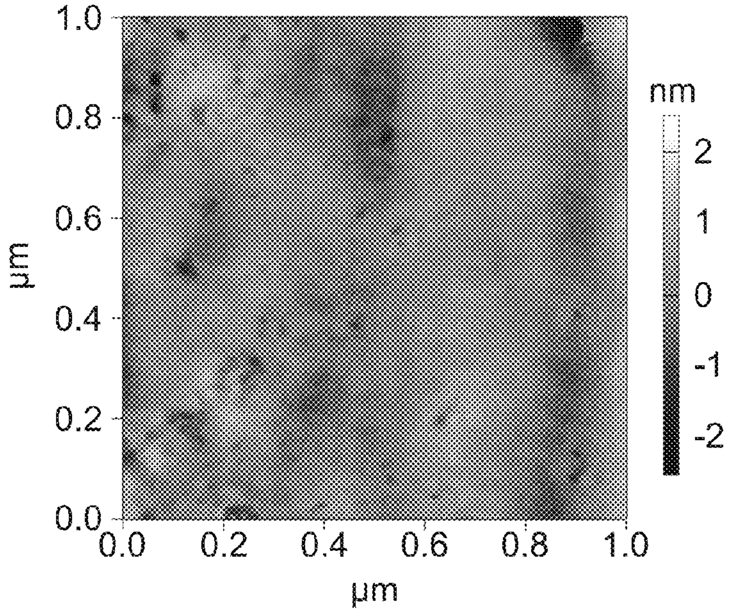

FIG. 5B is an AFM image of a surface of a PEC capsule. This sample was prepared with 4% by weight PEC solution.

Figure 6A:
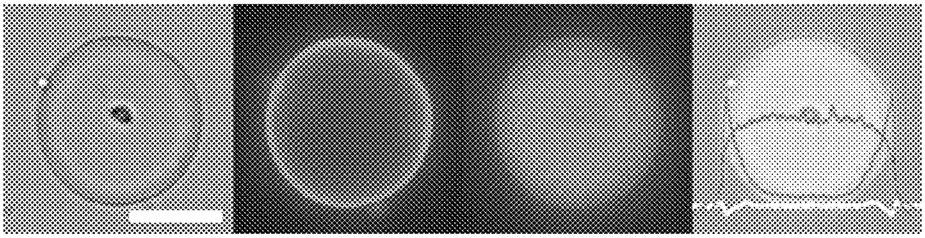
Figure 6B:
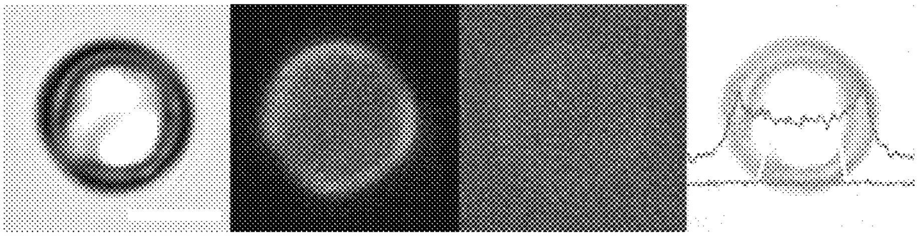
Figure 6C:
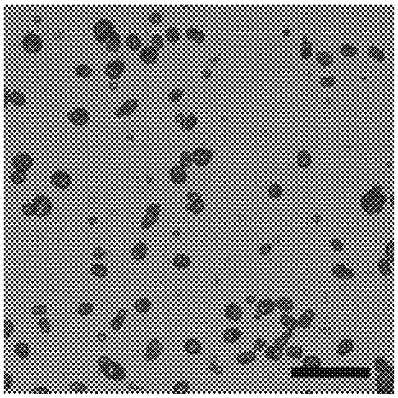
Figure 6D:
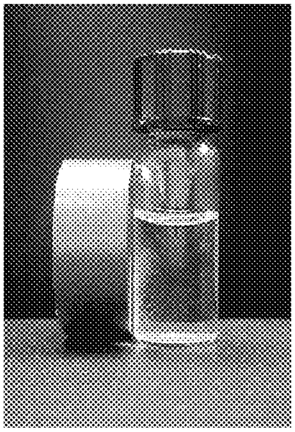

FIGS. 6A, 6B, and 6C are microscopy and fluorescence microscopy images of PEC microcapsules loaded with RB-D (FIG. 6A), Rubpy (FIG. 6B) and SPION (FIG. 6C). FIG. 6D is a photo of PEC microcapsules controlled by magnetic field. The scale bars are 10 (white) and 100 (black) μm.

DESCRIPTION OF THE EMBODIMENT(S) OF THE INVENTION

One aspect of the invention is a method of making a capsule comprising a polymer. According to the present invention, the polymer suitable for making a capsule is known as a "polyelectrolyte." A polyelectrolyte comprises multiple electrolytic repeat units that dissociate in solutions, making the polymer charged. The capsule of the present invention comprises a polyelectrolyte complex, that is, an intermolecular blend of a predominantly positively-charged polyelectrolyte and a predominantly negatively-charged polyelectrolyte.

In general, a polyelectrolyte complex is formed by combining a predominantly negatively charged polyelectrolyte and a predominantly positively charged polyelectrolyte. In some embodiments, the formation of complex to prepare the capsules starts with combining separate solutions, each containing one of the polyelectrolytes. Accordingly, in some embodiments, at least one solution comprises at least one predominantly positively-charged polyelectrolyte, and at least one separate solution comprises at least one predominantly negatively-charged polyelectrolyte. The formation of a polyelectrolyte complex ion pair, $Pol^+Pol^-$, by mixing individual solutions of the polyelectrolytes in their respective salt forms, $Pol^+A^-$ and $Pol^-M^+$, may be represented by the following equation (1):

$$Pol^+A^- + Pol^-M^+ \rightarrow Pol^+Pol^- + MA \quad (1)$$

where $M^+$ is a salt cation, such as sodium, and $A^-$ is a salt anion such as chloride. $Pol^-$ and $Pol^+$ represent repeat units on predominantly negatively charged and predominantly positively charged polyelectrolytes, respectively. According to the equation, the process of complexation releases salt ions into external solution, which are then part of the salt solution concentration.

The precipitates of polyelectrolyte complex, $Pol^+Pol^-$, formed by the reaction above are usually loose with much entrained water. The precipitates may be allowed to densify or consolidate further by sitting for a period of time, or being mechanically worked. The material that is comprises loose polyelectrolyte complex comprising a significant amount of entrained water may be termed a "starting polyelectrolyte complex."

Separate solutions containing the polyelectrolytes are preferably combined in a manner that allows the positively-charged polyelectrolyte(s) and the negatively-charged polyelectrolyte(s) to intermix. Intermixing the respective polyelectrolytes causes the in situ formation of a polyelectrolyte complex comprising an intermolecular blend of the positively-charged polyelectrolyte and the negatively-charged polyelectrolyte.

Individual polyelectrolyte solutions that are mixed may themselves comprise mixtures of polyelectrolytes of different chemical composition and/or molecular weight. For example, a solution may comprise two or more positive polyelectrolytes with two or more distinct chemical compositions. When the mixture of two or more positive polyelectrolytes is mixed with the negative polyelectrolyte solution the resulting complex will incorporate a blend of the two or more positive polyelectrolytes. Such a strategy is described for example in U.S. Pat. No. 7,722,752. Alternatively, the polyelectrolyte solution may comprise two or more negative polyelectrolytes with two or more distinct chemical compositions. Still further, one solution may comprise two or more positive polyelectrolytes with two or more distinct chemical compositions may be mixed with a separate solution comprising two or more negative polyelectrolytes with two or more distinct chemical compositions.

The starting polyelectrolyte complex is preferably prepared by mixing approximately stoichiometric amounts of positive and negative polyelectrolytes. In other words, the total number of positive polyelectrolyte charges within the starting polyelectrolyte complex is approximately equal to the total number of negative polyelectrolyte charges. The starting polyelectrolyte complex can be slightly non-stoichiometric, but preferably the ratio of total positive to negative charges in the starting polyelectrolyte complex is between 0.8 and 1.2, where a ratio of 1.0 is exactly stoichiometric.

A. Polyelectrolytes for Complexes

In some embodiments, the charged polymers (i.e., polyelectrolytes) used to form the complexes are hydrophilic, i.e., water soluble. In some embodiments, the charged polymers (i.e., polyelectrolytes) used to form the complexes are hydrophobic, i.e., organic soluble. The charged polymers comprise one or more monomer repeat units that are positively charged or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte of the present invention is predominantly positively charged or predominantly negatively charged and hereinafter is referred to as a "positively charged polyelectrolyte" or a "negatively charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). In some embodiments, a positively-charged polyelectrolyte has an average charge per repeat unit between 0 and 1 and a negatively-charged polyelectrolyte has an average charge per repeat unit between 0 and −1. Still further, in some embodiments, the polyelectrolyte may comprise repeat units having multiple charges, thereby enabling polyelectrolytes having average charge per repeat units above 1 (for positively charged polyelectrolytes) or less than −1 (for negatively charged polyelectrolytes). An example of a positively-charged copolymer is PDADMA-co-PAC (i.e., poly (diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive repeat units and negative repeat units distributed throughout the polymer in a random, alternating, or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero. If charges on one amphiphilic polymer associate with charges on another the material is considered a polyelectrolyte complex.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic.

Since the role of zwitterions groups is to reduce fouling of a polyelectrolyte complex, the location of the zwitterion groups within a polyelectrolyte capsule is preferably at the outer surface.

The charges on a polyelectrolyte may be derived directly from the monomer units, or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about 0.8.

Examples of a negatively-charged synthetic polyelectrolyte include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly (ether ether ketone) (SPEEK), poly(ethylenesulfonic acid), poly(methacryloxyethylsulfonic acid), their salts, and copolymers thereof; polycarboxylates such as poly(acrylic acid) (PAA) and poly(methacrylic acid), polyphosphates, and polyphosphonates.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH), polyvinylamine, polyethyleneimine (PEI); polysulfoniums, and polyphosphoniums.

Exemplary polyelectrolyte repeat units, both positively charged and negatively charged, are shown in Table I.

TABLE I

| Polyelectrolyte Repeat Units | |
|---|---|
| Name | Structure |
| diallyldimethylammonium (PDADMA) | 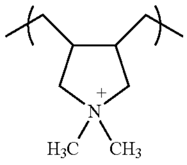 |
| styrenesulfonic acid (PSS) | 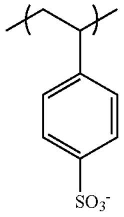 |
| N-methyl-2-vinyl pyridinium (PM2VP) | 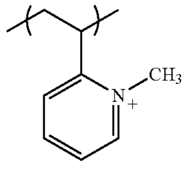 |
| N-methyl-4-vinylpyridinium (PM4VP) | 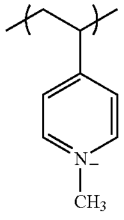 |

TABLE I-continued

| Polyelectrolyte Repeat Units | |
|---|---|
| Name | Structure |
| N-octyl-4-vinylpyridinium (PNO4VP) | 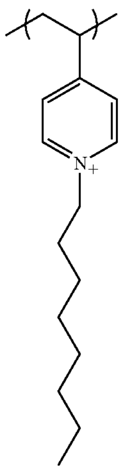 |
| N-methyl-2-vinyl pyridinium-co-ethyleneoxide (PM2VP-co-PEO) | 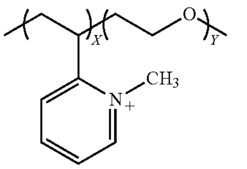 X and Y denote proportions of repeat units |
| acrylic acid (PAA) | 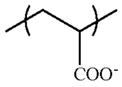 |
| Allylamine (PAH) | 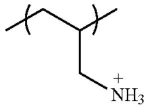 |
| ethyleneimine (PEI) | 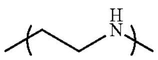 |

Further examples of polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule usually comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, glycosaminoglycans, alginic acid, chitosan, chitosan sulfate, cellulose sulfate, polysaccharides, dextran sulfate, carrageenan, glycosaminoglycans, sulfonated lignin, and carboxymethylcellulose.

The advantages of these naturally occurring polyelectrolytes are that they may be inexpensive, widely available, and nontoxic. The disadvantages of these naturally occurring polyelectrolytes are that their complexes can be soft and hydrated and they may be degraded or consumed by natural organisms. For capsules designed for pharmaceutical applications polyelectrolytes approved for ingestion or in vivo circulation are preferred.

In some applications it is desired that capsules degrade or break down after being ingested or when introduced in vivo. Such degradation may occur through hydrolysis of the polyelectrolytes or by the breakdown of chemical crosslinks holding them together. Examples of elements that can be broken down in vivo include disulfide bonds, ester groups and any functionality for which there is an enzyme capable of breaking or lysing or hydrolyzing parts of the molecule.

Natural, or biological, polyelectrolytes typically exhibit greater complexity in their structure than synthetic polyelectrolytes. For example, proteins may comprise any combination of about 2 dozen amino acid building blocks, some charged, which are natural repeat units. Polymeric nucleic acids such as DNA and RNA may also comprise many different monomer repeat units ("nucleobases"). The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte solutions that are mixed to prepare the starting polyelectrolyte complex typically comprise about 0.01% by weight to about 50% by weight of a polyelectrolyte, and preferably about 1% by weight to about 20% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention. Block polyelectrolytes, wherein a macromolecule comprises at least one block of charged repeat units, are also suitable. The number of blocks may be 2 to 5. Preferably, the number of blocks is 2 or 3. If the number of blocks is 3 the block arrangement is preferably ABA.

Many of the foregoing polyelectrolytes have very low toxicity. For example, poly(diallyldimethylammonium chloride), poly(2-acrylamido-2-methyl-1-propane sulfonic acid) and their copolymers are used in the personal care industry, e.g., in shampoos. Also, because the preferred polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Even if polyelectrolyte complexes are prepared by mixing organic-soluble and water-soluble polymers, the starting polyelectrolyte complex is preferably rinsed to remove organic solvents before it is processed according to the method described herein. Some organic solvents are hard to remove even with extensive rinsing. Therefore, the preferred solvent for polyelectrolyte complexation is water.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride), polyvinylamine and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonates), poly(diallyldimethylammonium), poly(N-alkylvinylpyridinium), poly(alkylimidazoles), poly(vinylbenzylalkylammoniums) and poly(ethyleneimine) where the small inorganic counterion, such as, sodium, potassium, chloride or bromide, has been replaced by a hydrophobic counterion such as tetrabutyl ammonium, tetraethyl ammonium, tetraalkylammonium, alkylammonium, alkylphosphonium, alkylsulfonium, alkylimidazolium, alkylpiperidinium, alkylpyridinium, alkylpyrazolium, alkylpyrrolidinium, iodine, alkylsulfate, arylsulfonates, hexafluorophosphate, tetrafluoroborate, trifluoromethane sulfonate, hexfluorphosphate or bis(trifluoromethane)sulfonimide.

Some polyelectrolytes comprise rigid rod backbones, such as aromatic backbones, or partially aromatic backbones, including sulfonated polyparaphenylene, sulfonated polyetherether ketones (SPEEK), sulfonated polysulfones, sulfonated polyarylenes, sulfonated polyarylene sulfones, and polyarylenes comprising alkylammonium groups.

The charged polyelectrolyte may be a synthetic copolymer comprising pH sensitive repeat units, pH insensitive repeat units, or a combination of pH sensitive repeat units and pH insensitive repeat units. pH insensitive repeat units maintain the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte at the surface of, or within, a polyelectrolyte complex.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly(acrylic acids), poly(methacrylic acids), poly(carboxylic acids), and copolymers thereof. Additional preferred polyelectrolytes comprise protonatable nitrogens, such as poly(pyridines), poly(imidazoles), poly(piperidines), and poly(amines) bearing primary, secondary or tertiary amine groups, such as poly(vinylamines) and poly(allylamine).

A capsule comprising polyelectrolyte complex comprising polyelectrolytes comprising a pH sensitive polyelectrolyte may be decomposed in full or in part by a change in pH. For example, a capsule comprising carboxylic polymers made at a pH greater than the pKa of the polymer (ca 5) will decompose or lose structural integrity at a lower pH, thereby releasing the contents of the capsule. Such a capsule ingested at neutral pH (7) will decompose in the stomach, with a pH<2.

To decrease or slow down disruption and possible decomposition of the polyelectrolyte complex capsule, polyelectrolytes comprising pH sensitive repeat units additionally comprise pH insensitive charged functionality on the same molecule. In one embodiment, the pH insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety ($—N^+R_aR_bR_c$ wherein $R_a$, $R_b$, and $R_c$ are independently alkyl, aryl, or mixed alkyl and aryl), a pyridinium moiety, a bipyridinium moiety or an imidazolium moiety, the sulfonium atom may be part of a sulfonium moiety ($—S^+R_dR_e$ wherein $R_d$ and $R_e$ are independently alkyl, aryl, or mixed alkyl and aryl) and the phosphonium atom may be part of a phosphonium moiety ($—P^+R_fR_gR_h$ wherein $R_f$, $R_g$, and $R_h$ are independently alkyl, aryl, or mixed alkyl and aryl). In another embodiment, the pH insensitive repeat unit is a negatively charged repeat unit selected from the group consisting of repeat units containing a sulfonate ($—SO_3^-$), a phosphate ($—OPO_3^-$), or a sulfate ($—SO_4^-$).

Exemplary negatively charged pH insensitive charged repeat units include styrenesulfonic acid, 2-acrylamido-2-methyl-1-propane sulfonic acid, sulfonated lignin, ethylenesulfonic acid, methacryloxyethylsulfonic acid, sulfonated ether ether ketone, phosphate. Preferred pH insensitive negatively charged polyelectrolytes include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof.

Exemplary positively charged pH insensitive repeat units include diallyldimethylammonium, vinylbenzyltrimethylammonium, vinylalkylammoniums, ionenes, acryloxyethyltrimethyl ammonium chloride, methacryloxy(2-hydroxy) propyltrimethyl ammonium, N-methylvinylpyridinium, other N-alkylvinyl pyridiniums, a N-aryl vinyl pyridinium, alkyl- or aryl imidazolium, sulfonium, or phosphonium. Preferred pH insensitive positively-charged polyelectrolytes comprising a quaternary ammonium group, such as poly (diallyldimethylammonium chloride) (PDADMA), poly(vinylbenzyltrimethylammonium) (PVBTA), poly(alkyammoniums), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof.

For illustrative purposes, certain of the pH insensitive positively-charged moieties are illustrated below:

Pyridinium having the structure:

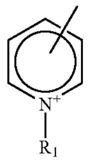

wherein $R_1$ is optionally substituted alkyl, aryl, alkaryl, alkoxy or heterocyclo. Preferably, $R_1$ is alkyl or aryl, and still more preferably $R_1$ is methyl;

Imidazolium having the structure:

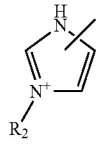

wherein $R_2$ is optionally substituted alkyl, aryl, alkaryl, alkoxy or heterocyclo. Preferably, $R_2$ is alkyl or aryl, and still more preferably $R_2$ is methyl;

The pH insensitive polyelectrolyte may comprise a repeat unit that contains protonatable functionality, wherein the functionality has a pKa outside the range of experimental use. For example, poly(allylamine) has protonatable amine functionality with pKa in the range 8-10, and is thus fully charged (protonated) if the experimental conditions do not surpass a pH of about 7.

Preferably, the pH insensitive groups constitute about 10 mol % to about 100 mol % of the repeat units of the polyelectrolyte, more preferably from about 20 mol % to about 80 mol %. Preferably, the pH sensitive groups constitute about 30 mol % to about 70 mol % of the repeat units of the polyelectrolyte.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table II. Preferred uncharged repeat units also include N-isopropylacrylamide and propylene oxide.

TABLE II

| Neutral Repeat Units | |
|---|---|
| Name | Structure |
| Acrylamide | 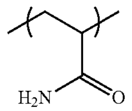 |
| Vinylpyrrolidone | 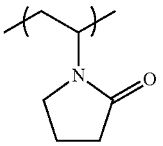 |
| Ethylene oxide | 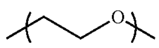 |
| Vinylcaprolactam | 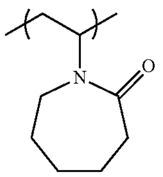 |

Adsorption is driven by the net influence of various interdependent interactions between and within surfaces and biopolymer. Possible polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, adsorbers such as proteins are remarkably tenacious, due to the other interaction mechanisms at their disposal. It is an object of this invention to show how surfaces may be selected to encourage or discourage the adsorption of proteins to polyelectrolyte complex capsules when they are used in vivo or in natural environments. Protein adsorption may be discouraged by incorporating, preferably at the external surface, polyelectrolytes comprising repeat units having hydrophilic groups and/or zwitterionic groups.

Polyelectrolyte complexes comprising zwitterions useful for preventing protein and/or cell adhesion have been described in U.S. Publication No. 2005/0287111, which is hereby incorporated by reference as if set forth in its entirety. It has been found that polymers comprising zwitterionic functional groups alone do not form polyelectrolyte complexes if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio]propane sulfonate) (PAEDAPS) and poly(N-propane sulfonate-2-vinyl pyridine) (P2PSVP). The structures of these zwitterions are shown in Table III. Examples of other suitable zwitterionic groups are described in U.S. Publication No. 2005/0287111.

TABLE III

| Zwitterionic Repeat Units | |
|---|---|
| Name | Structure |
| 3-[2-(acrylamido)-ethyldimethyl ammonio] propane sulfonate (AEDAPS) | 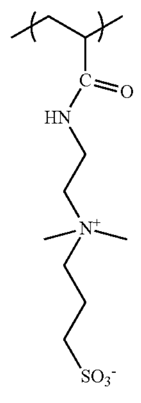 |

TABLE III-continued

| Zwitterionic Repeat Units | |
|---|---|
| Name | Structure |
| N-propane sulfonate-2-vinyl pyridine (2PSVP) | 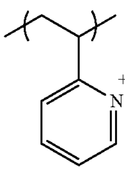 |

It has been disclosed (U.S. Publication No. 2005/0287111) that films of polyelectrolyte complex prepared by the multilayering method are able to control the adsorption of protein. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred moles ratio of charged to neutral repeat units in a polyelectrolyte complex is from 10:1 to 1:4, and a more preferred ratio is 5:1 to 1:2.

Ethylene oxide repeat units may also be employed in comb polymers, preferably with a main, charged chain comprising a plurality of at least one of the charged repeat units listed previously and oligomers or polymers of ethylene oxide units grafted to this main chain. Such an architecture is termed a comb polymer, where the charged backbone represents that backbone of the comb and the grafted ethylene oxide oligomers or polymers represent the teeth of the comb.

Preferably the location of the zwitterionic and/or polyethylene oxide repeat units is at the external surface of the polyelectrolyte complex capsule. In order to provide antibiofouling properties to the polyelectrolyte complex capsule the zwitterionic and/or polyethylene oxide repeat units are sorbed on the capsule after it is formed, for example by exposing the capsule to a solution comprising a polyelectrolyte comprising zwitterionic or ethylene oxide repeat units. Alternatively, the zwitterionic or ethylene oxide functionality can be chemically grafted to the surface of the polyelectrolyte complex capsule using chemical grafting or coupling methods.

In some applications the surface of the polyelectrolyte complex capsule is rendered bioadhesive, for example by the sorption of peptides (synthetic or natural) or proteins, such as fibronectin, comprising the RGD sequence of amino acids, as disclosed in U.S. Publication No. 2003/0157260 and U.S. Pat. No. 6,743,521. In other embodiments the surface of the polyelectrolyte complex capsule comprises 3,4-dihydroxyphenylalanine (DOPA) or catechol units, which are known to be bioadhesive. In further embodiments the surface of the polyelectrolyte complex capsule further comprises reactive functional groups, such as aldehydes, ketones, carboxylic acid derivatives, anhydrides (e.g., cyclic anhydrides), alkyl halides, acyl azides, isocyanates, isothiocyanates, and succinimidyl esters. These groups react with amine groups found in biological tissue. Thus, an article comprising said groups adheres to tissue.

In one preferred embodiment, chemical crosslinking is introduced into the polyelectrolyte complex capsule for stability and toughness. After forming the capsule it may be treated with a difunctional crosslinking agent, such as $XCH_2$-φ-$CH_2X$, where X is a halogen (Cl, Br, or I) and φ is a phenyl group. The phenyl group may be replaced by another aromatic or aliphatic moiety, and easily-diplaceable groups, such as toluene sulfonate, may replace the halogen. A preferred crosslinking agent is a dihalogenated compound, such as an aromatic or aliphatic dibromide, which is able to alkylate residual unalkylated units on two adjoining polyelectrolyte chains.

Another preferred method of chemical crosslinking a polyelectrolyte complex capsule is heat treatment. For example, Dai et al. (*Langmuir* 17, 931 (2001)) disclose a method of forming amide crosslinks by heating a polyelectrolyte multilayer comprising amine and carboxylic acid groups. Optionally, the carboxylic acid groups may be activated by transforming them into acid chlorides or anhydrides. Yet another preferred method of introducing crosslinking, disclosed by Kozlovskaya et al. (Macromolecules, 36, 8590 (2003)) is by the addition of a carbodiimide, which activates chemical crosslinking. The level of chemical crosslinking is preferably 0.01% to 50%, and more preferably 0.1% to 10%.

Another method of chemical crosslinking of a polyelectrolyte complex capsule is by photocrosslinking. Photocrosslinking may be achieved by the light-induced decomposition or transformation of functional groups, such as diarylbenzophenones, that form part of the polymer molecules. See, for example, Strehmel, Veronika, "Epoxies: Structures, Photoinduced Cross-linking, Network Properties, and Applications"; Handbook of Photochemistry and Photobiology (2003), 2, 1-110. See also Allen, Norman S., "Polymer photochemistry", Photochemistry (2004), 35, 206-271; Timpe, Hans-Joachim "Polymer photochemistry and photocrosslinking" Desk Reference of Functional Polymers (1997), 273-291, and Smets, G., "Photocrosslinkable polymers", Journal of Macromolecular Science, Chemistry (1984), A21 (13-14), 1695-703. Alternatively, photocrosslinking of a polyelectrolyte complex may be accomplished by infusing the formed polyelectrolyte complex capsule with a small photoactive crosslinker molecule, such as diazidostilbene, then exposing the polyelectrolyte complex to light.

In some embodiments, the polyelectrolyte complex comprises further physical crosslinks created by hydrogen bonding. Hydrogen bonding is weaker than chemical bonding and occurs between a hydrogen bond donor and a hydrogen bond acceptor. Hydrogen bonds are minimally impacted by the presence of salt and thus the level of physical crosslinking due to hydrogen bonding remains substantially the same as the salt concentration is varied. Accordingly, the polyelectrolyte complex capsules further comprise polymer repeat units capable of hydrogen bonding. Examples of hydrogen bond donor/acceptor pairs are presented in U.S. Pat. Nos. 6,740,409 and 7,470,449 as well as U.S. Publication No. 2005/0163714, each of which is hereby incorporated by reference as if set forth in their entireties.

According to some embodiments of the present invention, a positively charged polyelectrolyte and a negatively charged polyelectrolyte are dissolved in a polyelectrolyte solution. The polyelectrolyte solution additionally comprises a solvent. The solvent may be selected from the group consisting of water, acetone, ethanol, methanol, trifluoroethanol, and any combination thereof.

In some embodiments, the polyelectrolyte solution comprises the dissolved positively charged polyelectrolyte at a concentration between about 1% by weight and about 10% by weight and further comprises the dissolved negatively charged polyelectrolyte at a concentration between about 1% by weight and about 10% by weight. In some embodiments, the polyelectrolyte solution comprises the dissolved positively charged polyelectrolyte at a concentration between about 1% by weight and about 5% by weight and further comprises the dissolved negatively charged polyelectrolyte at a concentration between about 1% by weight and about 5% by weight. In some embodiments, the polyelectrolyte solution comprises the dissolved positively charged polyelectrolyte at a concentration between about 5% by weight and about 10% by weight and further comprises the dissolved negatively charged polyelectrolyte at a concentration between about 5% by weight and about 10% by weight.

According to some embodiments of the present invention, a positively charged polyelectrolyte and a negatively charged polyelectrolyte are loosely blended together to form a coacervate. The coacervate additionally comprises a solvent. The solvent may be selected from the group consisting of water, acetone, ethanol, methanol, trifluoroethanol, and any combination thereof. The coacervate may comprise between about 1% by weight and about 10% by weight positively charged polyelectrolyte and between about 1% by weight and about 10% by weight negatively charged polyelectrolyte. In some embodiments the coacervate may comprise between about 1% by weight and about 5% by weight positively charged polyelectrolyte and between about 1% by weight and about 5% by weight negatively charged polyelectrolyte. In some embodiments, the coacervate may comprise between about 5% by weight and about 10% by weight positively charged polyelectrolyte and between about 5% by weight and about 10% by weight negatively charged polyelectrolyte.

B. Doping Level

Doping of the polyelectrolyte complex affects the elastic and dynamic mechanical properties of the polyelectrolyte complex, such as, for example, the elastic and complex shear modulus.

In some embodiments, the polyelectrolyte solution further comprises at least one dissolved salt, or comprises two or more dissolved salts. It has been observed that doping by increasing the salt concentration decreases the modulus of a polyelectrolyte complex, G, which is the shear modulus or modulus or rigidity. Conversely, decreasing the salt concentration increases G, making the complex stiffer.

The process of doping is defined as the breaking of polymer/polymer ion pair crosslinks by salt ions entering the polyelectrolyte complex, i.e., the opposite of Equation (1). Salt ions electrically compensate the charges on the polyelectrolytes. In such compensation, the salt ions are termed counterions and are paired with polyelectrolyte repeat units of opposite charge. Salt ions residing in pores or paired with other salt ions or present as crystals are not considered to be doping the polyelectrolyte complex and do not contribute to the doping level. The level or density of doping is therefore inversely related to the crosslink density. The breaking of ion pair crosslinks by doping is reversible and under thermodynamic control. In contrast, chemical crosslinks are usually irreversible.

The doping level of polyelectrolyte complexes is created and maintained by contacting the starting polyelectrolyte complex with a solution comprising salt ions of a specific concentration. Equilibration of the polyelectrolyte complex in the salt solution in which the complex is immersed may be fairly rapid, with durations typically on the order of between about 10 minutes and about 60 minutes per millimeter thickness of the polyelectrolyte complex article.

The extent to which ion pair crosslinks have been replaced by salt counterions within the bulk of the article comprising polyelectrolyte complex may be quantified in terms of a doping level or doping level ratio, determined by dividing the sum of the ionic charge provided by salt ions acting as polyelectrolyte counterions by the sum of charge provided by the polymer repeat units. This ratio may be expressed in terms of a doping level percentage by multiplying the doping level ratio by 100. The lowest doping level is 0.000 (0%) wherein all the positively charged polyelectrolyte repeat units are paired with all the negatively charged polyelectrolyte repeat units, which corresponds to the maximum level (100%) of ionic crosslinking. The highest doping level is 1.00 (100%), where all charged polyelectrolyte repeat units are paired with a salt ion. At a doping level of 1.00, or 100%, the polyelectrolyte complex is dissolved, or maintained in solution, as described in U.S. Pat. No. 3,546,142. Dissolved polyelectrolyte complexes are preferred for the present invention.

The doping level of a stoichiometric (1:1) polyelectrolyte complex is the fraction of polymer/polymer ion pairs which have been broken.

The doping level can be measured, for example infrared absorption spectroscopy (see. Farhat and Schlenoff, *Langmuir* 2001, 17, 1184; and Farhat and Schlenoff, *Journal of the American Chemical Society,* 2003, vol. 125, p. 4627) has been used to measure doping levels below about 0.5.

To illustrate a doping level calculation, suppose that a simple polyelectrolyte complex comprises a blend of one positively charged polyelectrolyte having 100 positively charged repeat units paired with one negatively charged polyelectrolyte having 100 negatively charged repeat units. Such a polyelectrolyte complex therefore has a total charge provided by the charged repeat units of 200. The maximum number of ionic crosslinks, or polymer/polymer ion pairs, is 100. This polyelectrolyte complex may be doped with salt ions which become associated with the charged repeat units. For example, if 10 sodium ions are associated with 10 negatively charged repeat units and 10 chloride ions are associated with 10 positively charged repeat units, the sum of charges provided by the salt ions is 20, and 10 ionic crosslinks have been broken. The doping level is a ratio calculated by dividing the sum of charges of the salt ions paired with polyelectrolytes by the sum of charges from the repeat units, i.e., 20/200=0.1, or 10%, stated as a doping level percentage. By way of further example, if 5 calcium ions (charge 2+) are associated with 10 negatively charged repeat units and 10 chloride ions are associated with 10 positively charged repeat units, the sum of charges provided by the salt ions is 20 (=5×2 for the calcium+10 for the chloride) and the doping level ratio is 20/200=0.1, or 10%, stated as a doping level percentage. To achieve these doping levels, the article comprising the polyelectrolyte is preferably maintained in contact with a solution of the doping salt in water.

At a doping level greater than about 0.7 the complex begins to form an elastic liquid known as a polyelectrolyte coacervate. A coacervate is a loosely-bound viscoelastic blend, so it is not quite a solution of dissolved polyelectrolyte. The more salt that is added the lower the viscosity becomes. At a high enough doping level, e.g., about 1.00, the polyelectrolytes are separated from each other and form a solution in which both the positively charged polyelectrolyte and the negatively charged polyelectrolyte are dissolved.

According to the present invention, the doping level is preferably sufficiently high to reduce the viscosity of the polyelectrolyte complex solution to a value lower than about 1000 poise, such as between about 1 poise and about 1000 poise, at room temperature. In some embodiments, the viscosity of the polyelectrolyte complex solution is less than about 10,000 cP, at room temperature.

At these viscosities the complex has liquid-like properties and may be sprayed by any one of a number of spraying methods known to be useful for liquids. Accordingly, the preferred level of doping of the polyelectrolyte complex is between 0.90 and 1.00, more preferably between 0.95 and 1.00. The most preferred doping level is 1.00, i.e., when the polyelectrolytes are separated from each other and form a solution.

C. Salt Ions

In some embodiments, the polyelectrolyte solution further comprises at least one dissolved salt, or comprises two or more dissolved salts. In some embodiments, the dissolved salt concentration in the polyelectrolyte solution is between about 0.1M (molar) and about 5M (molar), such as between about 0.2M and about 4M, or between about 1M and about 4M, such as between about 2M and about 4M, or between about 0.2M and about 1M. A wide variety of salt ions may be added to the polyelectrolyte complex to dope the starting polyelectrolyte complex. In general, the salt may comprise any cation selected from among the alkali metal cations, alkaline earth metal cations, transition metal cations, semimetallic cations, and organic cations such as amines or quaternary ammoniums. The salt(s) may comprise a mixture of two or more of any of these cations. Among the alkali metal cations, lithium, sodium, potassium, and rubidium may be incorporated into the polyelectrolyte complex, with sodium and potassium being particularly preferred. In certain physiological applications, the choice of alkali metal cations may be limited to sodium or potassium ions. Among the alkaline earth metal cations, magnesium, calcium, strontium, and barium may be incorporated into the polyelectrolyte complex. Calcium and magnesium cations are particularly preferred, and for physiological applications, the choice of alkaline earth metal cations may be limited to calcium and magnesium. A wide variety of transition metals may be incorporated into the polyelectrolyte complex including scandium, yttrium, titanium, zirconium, vanadium, niobium, chromium, molybdenum, manganese, iron, ruthenium, cobalt, rhodium, nickel, palladium, platinum, copper, silver, gold, and zinc. In certain physiological applications, the choice of transition metal cations may be limited to zinc, iron, and copper. Other metal cations that may be incorporated into the extruded articles include aluminum, indium, tin, lead, and bismuth. Organic cations that may be included include ammonium, primary, secondary, and tertiary amines, and quaternary ammoniums comprising alkyl groups having from one to eight carbon atoms. Primary amines, secondary amines, and tertiary amines are protonated to achieve positive charge and are thus pH sensitive. Exemplary primary amines, secondary amines, and tertiary amines are protonated forms of methylamine, dimethylamine, trimethyl amine, ethylamine, diethylamine, and triethylamine among others. Quaternary amines are pH insensitive groups. Exemplary quaternary amines include tetramethylammonium, tetraethylammonium, tetrapropylammonium, among others. In one embodiment, the amine is a linear polyamine such as ethylene diamine, diethylene triamine, dipropylene triamine, triethylene tetraamine, tripropylene tetraamine, tetraethylene pentaamine, tetrapropylene pentaamine, spermine, or spermidine.

The anion may be selected from among halide anions, oxoanions, and organic anions. A combination of anions may be incorporated into the polyelectrolyte complex. Halide ions that may be incorporated into the polyelectrolyte complex include fluoride, chloride, bromide, and iodide. In one preferred embodiment, the halide anion is bromide ion. Oxoanions that may be incorporated into the polyelectrolyte complex include sulfonate, sulfate, sulfite, phosphate, phosphite, phosphonate, pyrophosphate, hypochlorite, chlorite, chlorate, perchlorate, iodate, periodate, bromate, borate, carbonate, nitrate, nitrate, aluminate, and manganate, among others. Organic anions that may be incorporated into the polyelectrolyte complex include carboxylates, such as citrate, lactate, acetate, benzoate, formate, malate, malonate, fumarate, oxalate, propionate, butyrate, tartrate, and valerate, phthalate, among others. Hydrophobic anions, such as those with a high hydrocarbon to charge ratio, are preferred for enhancing doping. Preferred organic anions for physiological applications include citrate and lactate. Organic solvent is optionally added to the aqueous salt solution.

Other preferred salts include chloride salts, citrate salts, and phosphate salts. Preferred chloride salts include sodium chloride, potassium chloride, magnesium chloride, calcium chloride, and aluminum chloride. Preferred citrate salts include trisodium citrate, disodium hydrogencitrate, sodium dihydrogencitrate, tripotassium citrate, dipotassium hydrogencitrate, potassium dihydrogencitrate, magnesium citrate, and calcium citrate. Preferred phosphate salts include trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, and magnesium phosphate.

In general, it has been found that the higher the charge on the ion the more effectively it dopes the polyelectrolyte complex (PEC). Thus, double-charged ions such as calcium are more effective than single-charged ions such as sodium. Triple-charged ions are even more effective.

In view of the above cations and anions, a wide variety of salts may be used to dope the polyelectrolyte complex starting material for the purpose liquefying it. Preferably, the salts are soluble in aqueous solution at a concentration at least sufficient to incorporate ions into the polyelectrolyte complex starting material to an extent sufficient to achieve the doping level needed for the desired viscosity.

Low viscosity, highly fluid doped polyelectrolyte complex in water, formed, for example, by adding salt solution to the starting polyelectrolyte complex, is herein termed "the polyelectrolyte complex dope" or simply "the dope". While the preferred method of preparing the dope is to contact the starting polyelectrolyte complex with a salt solution, it is also possible to prepare the dope by adding the individual polyelectrolyte components to the salt solution. The eventual composition is comparable. For example, to a concentrated salt solution, solutions of positive polyelectrolyte and negative polyelectrolyte are added. Alternatively, concentrated salt can be added to the solutions of polyelectrolyte before they are mixed. Said solutions of polyelectrolyte, with or without salt, may be added simultaneously or sequentially. The dope contains a fluid polyelectrolyte complex or, preferably, dissolved polyelectrolyte. The advantages of preparing a starting polyelectrolyte, then doping it to the desired level, are twofold: first, on precipitating the complex, small molecule impurities, such as residual monomers, are left behind in the supernate, leading to a purer complex. Second, when polyelectrolytes are mixed to form the complex the precipitated complex is usually close to stoichiometric. Thus, if the starting polyelectrolyte complex is dried, powdered, and used as starting material for preparing the dope, the composition is known to be close to 1:1.

The dope may optionally comprise organic solvent such as ethanol. Such organic solvents may assist in dissolving the polyelectrolyte complex, i.e., providing a solution of polyelectrolyte complex with doping level 1.00. If an organic solvent is to be used as a co-solvent with water, the organic solvent preferably has low toxicity.

There are several methods to establish whether the solution comprises a complex, wherein the doping level is less than 1.00, or, in fact, comprises dissolved polyelectrolyte, wherein the doping level is 1.00. The first method is to vary the salt concentration and measure the viscosity. If the viscosity changes strongly with salt concentration, the doping level is less than 1.00. If the viscosity changes weakly with salt concentration, the doping level is 1.00. An example of this difference is provided below.

The preferred method of spraying employs any spraying technique known to the art such as spraying using compressed air, entrainment of the liquid by spraying using a carrier gas, ultrasonic spraying, or misting.

The viscosity is preferably measured at room temperature using a device known to the art such as a viscometer or a rheometer. Units of viscosity vary. Some conversions are as follows: 100 Centipoise (cP)=1 Poise; 1 Centipoise=1 mPa s (Millipascal Second); 1 Poise=0.1 Pa s (Pascal Second); Centipoise=Centistoke×Density.

The preferred viscosity is optimized to allow the dope to be sprayed effectively by the particular spraying method chosen. Some methods are suited to different viscosity ranges than others. Water has a viscosity of around 1 cP. SAE motor oil around 600 cP; honey around 10,000 cP; peanut butter around 250,000 cP. The preferred viscosity for spraying in less than 10,000 cP, preferably less than 1000 cP and more preferably less than 100 cP.

Undoped polyelectrolyte complexes are obtained by soaking polyelectrolyte complexes in water.

D. Methods of Forming the Capsules

In the preferred method of forming capsules the dope is sprayed into a liquid receiving bath, e.g., an aqueous solution, under conditions optimized to produce capsules. In some embodiments, the liquid receiving bath comprises a liquid selected from the group consisting of water, an organic solvent, and a combination thereof. In some embodiments, the liquid receiving bath comprises the same liquid used to dissolve the polyelectrolyte complex. Accordingly, the liquid receiving bath may comprise solvent selected from the group consisting of water, acetone, ethanol, methanol, trifluoroethanol, and any combination thereof. In some embodiments, the liquid receiving bath comprises a different liquid compared to the liquid used to dissolve the polyelectrolyte complex. In some embodiments, the liquid receiving bath further comprises dissolved salt. The dissolved salt may be any of the salts listed above in connection with the polyelectrolyte solution. Preferably, the salt concentration of the liquid receiving bath is less than the salt concentration of the polyelectrolyte complex solution. The dissolved salt concentration in the liquid receiving bath may be between about 0.01M and about 1M, such as between about 0.01M and about 0.5M, such as between about 0.01M and about 0.2M, or between about 0.5M and about 1M, or between about 0.01M and about 0.1M.

The production of capsules by spraying a polyelectrolyte complex dope into aqueous solution was discovered accidentally. In the majority of cases, spraying the dope into water produced particles of polyelectrolyte complex, as expected from Equation (1), as the water would dilute the salt concentration, leading to undoping and precipitation of solid complex. That precipitation under certain conditions might lead to spherical particles with well-defined cavities, i.e., capsules, was unexpected.

In the preferred method of forming the capsules the dope is sprayed via ultrasonic misting or spraying. Ultrasonic misting or ultrasonic spraying may be accomplished by use of an ultrasonic nozzle, which is a type of spray nozzle that uses high frequency sound waves, which create capillary waves in a liquid film. In some embodiments, the dope may be ultrasonically misted or ultrasonically sprayed into aqueous solution, which may be referred to as the receiving bath. Preferably, the receiving bath comprises lower concentrations of salt than the dope. In some embodiments, the salt concentration of the receiving bath less than about 0.5 M, such as less than about 0.1M.

Ultrasonic misting or spraying is preferred over spraying under hydraulic pressure from a nozzle because ultrasonic spraying typically creates smaller droplets, in the micrometer range, than pressure spraying. In addition, the low droplet velocity of ultrasonic spraying is thought to allow the droplet to enter the receiving bath more gently without deforming or breaking up.

Spraying by pressure entrainment with a gas is less preferred because of the high velocity of the droplets produced during the spraying and broad droplet distributions.

In some embodiments, pressure spraying or entrainment spraying may be employed. In such embodiments, it is preferable that the dope is pressure sprayed or entrainment sprayed at as low a droplet velocity as possible. The receiving bath is placed at a sufficient distance from the nozzle to allow the droplets to slow down before hitting the surface of the bath.

The receiving bath can be of any dimension suited to collecting the sprayed capsules. For example, the bath can be a container of aqueous solution or a sheet of aqueous solution flowing horizontally or vertically (as in a waterfall). To establish a sheet of flowing solution the liquid in the receiving bath is preferably recirculated via pumping. The volume of the bath is sufficient to prevent capsules from impinging on each other at the surface while they are sprayed. If droplets hit each other before the capsule has time to form the capsules will fuse together. Accordingly, the ratio of receiving bath volume to total sprayed volume is preferably greater that 10:1, preferably greater than 100:1.

The temperature of the solution to be sprayed and the receiving bath are advantageously controlled in order to optimize formation of the capsules. Temperature strongly affects the viscosity of the solution and the rate at which the capsules are formed once the droplets hit the receiving bath. In some embodiments, temperature may be optimized in order or provide the optimum particle size and wall thickness of the capsules, which depends on the application of the capsule. In some embodiments, the liquid receiving bath is maintained at a temperature between about 30° C. and about 90° C.

The polyelectrolyte concentration in the dope must be high enough to ensure the formation of capsule walls during precipitation of the polyelectrolyte complex. If the droplets enter the water bath quickly and maintain their integrity as the salt leaves the PEC quasi-spherical shapes should result. The key to obtaining capsules, rather than solid particles, is for the water/PEC interface to harden quickly while the PEC at the center of the droplet diffuses radially outwards, which produces a wall. Other factors that must be balanced are the outwards diffusion of ions versus the inrush of water under a strong osmotic pressure gradient. If the concentration of polyelectrolyte complex is too high solid particles result.

The preferred concentration of polyelectrolyte complex in the dope depends on molecular weight. For optimum capsule formation the concentration must be over the critical overlap concentration of polymer chains, φc, which is the solution concentration at which polymer chains begin to overlap with each other. The higher the molecular weight the lower the concentration of polymer needed for chain overlap. In the Example below, φc was estimated be about 3% by weight. At a concentration greater than φc solid polyelectrolyte complex can phase separate into a continuous phase because of this overlap. The formation of such a continuous phase makes it possible to obtain capsules with continuous walls instead of separated pieces. The signature of chain overlap is a stronger increase of viscosity with concentration, as seen in the Example below.

Optionally, the receiving bath comprises the same or a different, salt as the dope. For example, the dope could comprise KBr at a concentration of 1.9M and the rinse solution could comprise NaCl at 0.6M. The second salt concentration is insufficient to dope the complex to a high enough viscosity to assume liquid-like properties.

Nonstoichiometric complexes have excess counterions of one charge and are thus softer than stoichimetric counterions. Accordingly, the polyelectrolyte stoichiometry of the dope is preferably close to 1:1. Preferred ranges of stoichiometry are between about 0.9:1.1 positive to negative and about 1.1:0.9 positive to negative, and more preferred between about 0.95:1.05 positive to negative and about 1.05 to 0.95 positive to negative. In capsules where the stoichiometric ratio is other than 1:1, the stoichiometry may be adjusted towards 1:1 by treating the formed polyelectrolyte complex capsules with a solution of polyanion or polycation. For example, if the capsule is slightly rich in polycation, the capsule can be immersed in, or contacted with, a solution comprising polyanion and, optionally, a salt.

In some embodiments, the capsule may preferably be formed from a dope that is slightly nonstoichiometric. For example, if selective transport of negatively charged species encapsulated within the capsule is desired, the capsule wall should comprise a slight excess of positively charge polymer. In some embodiments, selective transport of positively charged species encapsulated within the capsule calls for a capsule wall comprising slight excess of negatively charge polymer. Accordingly, excess of positively or negatively charged polymer can be built into the capsule wall by employing a dope with a slight excess of positively charged polyelectrolyte or negatively charged polyelectrolyte, respectively, under the conditions of capsule formation (e.g., temperature and pH).

In some embodiments, the method of the present invention causes the formation of capsules in the receiving bath, the capsules being defined by a capsule wall. In some embodiments, the wall of the capsule has thickness between about 0.1 micrometers and about 100 micrometers, such as between about 0.1 micrometers and about 50 micrometers, or between about 50 micrometers and about 100 micrometers. In some embodiments, the capsule is spherocylinder in shape. The diameter of the spherocylinder capsule may be between about 0.1 micrometers and about 100 micrometers.

In some embodiments, a ratio of the diameter of the spherocylinder capsule to the thickness of the wall of the capsule is between 100 and 0.1. In some embodiments, the capsule is spherical in shape. The diameter of the spherical capsule may be between about 0.1 micrometers and about 100 micrometers. In some embodiments, a ratio of the diameter of the spherical capsule to the thickness of the wall of the capsule is between 100 and 0.1.

E. Additives

A wide variety of additives may be employed in the present invention. Preferably, additives are added to the dope before capsule formation. Optionally, additives are added to the receiving bath, but for most purposes this is an inefficient way of including additive in the final capsule. Additives may be inorganic or organic, polymeric or monomeric, charged or neutral, suspended or dissolved, bioactive, or nonbioactive. Either the wall or the cavity of the capsule, or both, may comprise the additive. The desired location of the additive depends on the function of the additive.

F. General Additives

Solid additives that may be incorporated into the polyelectrolyte complex are typically known to the art to modify the physical properties of materials. Additives are not considered in the doping calculations. The preferred weight % of metallic, mineral, polymer, or carbon additive is between 0.1% by weight and 90% by weight relative to the weight of polyelectrolytes. Additives include fillers and/or reinforcing agents and/or toughening agents, such as inorganic materials such as metal or semimetal oxide particles (e.g., silicon dioxide, aluminum oxide, titanium dioxide, iron oxide, zirconium oxide, and vanadium oxide), clay minerals (e.g., hectorite, kaolin, laponite, attapulgite, montmorillonite), hydroxyapatite or calcium carbonate. For example, nanoparticles of zirconium oxide added to an ultrathin film of polyelectrolyte complex improves the abrasion resistance of the film. See Rosidian et al., U.S. Pat. No. 6,316,084.

High aspect ratio fillers are preferred for stiffening or strengthening a capsule at a relatively low fill loading. Preferred high aspect ratio additives include metal fibers, inorganic platelets such as calcium carbonate or calcium phosphate (such as hydroxyapatite), needle-like clay minerals, such as attapulgite and halloysite, and carbon-based fibers such as carbon fibers or single or multiwalled carbon nanotubes or graphene. Other high aspect ratio materials having at least one dimension in the 1 nanometer to 100 micrometer range are suitable additives. Such high aspect ratio materials include cellulose nanofibers and cellulose nanocrystals. The weight % of additives in the dope depends on many factors, such as the aspect ratio and the degree of modification of physical properties required. Accordingly, the solid additives may comprise between about 1% by weight and 90% by weight of the dope.

Because of the high salt environment of the dope, additives may experience stability problems, such as agglomeration or precipitation. If such problems are encountered is it preferable to include stabilizers, such as sufactants or surface coatings, to stabilize the additive.

G. Bioactive Additives

For biomedical applications, such as the delivery of drugs or therapeutics, the cavity of the capsule preferably contains one or more bioactive species. Preferred bioactive species are antibiotics, antivirals, anticancer agents, DNA, RNA including siRNA, antibodies, aptamers, proteins, enzymes, carbohydrates, anti-inflammation, antirejection agents, growth factors, dietary supplements, biominerals, and any agent known to have beneficial effects on health when ingested or injected. Said additives are preferably added to the dope. Advantageously, the additive is entrapped in the capsule as soon as it is formed, which avoids the additional step of having to load the capsule post-formation. However, such loading is possible using methods known to the art such as described in De Geest et al Chem. Soc. Rev. 36, 636-649 (2007) and Becker et al. Small, 6, 1836-1852 (2010).

Examples of antibiotics are well known to the art and are to be found in E. M. Scholar, The Antimicrobial Drugs, New York, Oxford University Press, 2000 or the Gilbert et al., The Stanford Guide to Antimicrobial Therapy, Hyde Park, Vt., 2000, or the R. Reese, Handbook of Antibiotics, Philadelphia, Lippincot, 2000. Antibacterial agents include silver including silver nanoparticles. Other additives are known to the art for promoting various biomedical properties. These include paclitaxel, seratonin, heparin, and anticlotting factors. Unlike additives used to modify the physical properties of the polyelectrolyte complex article, additives with biological or biomedical activity are typically added in lower concentration. Accordingly, such additives preferably comprise between 0.0001% by weight (1 μg/g) and 5% by weight of the dope. The concentration of the additive is typically adjusted to obtain the optimum physiological response.

H. Bath Additives

The receiving bath optionally comprises additives intended to adsorb to the outer surface of the capsule. The purpose of these additives is to modify the interfacial properties of the capsules. Accordingly, species that impart biological selectivity or targeting of capsules may be present in the receiving bath. Examples of said species include antibodies, DNA, RNA, enzymes, aptamers and polysaccharides. Other additives for the receiving bath adsorb to the capsule and render it biocompatible. Examples of such additives include polymers comprising polyethylene glycol or polyethylene oxide and polymers comprising zwitterionic groups such as those disclosed above. While the surface of the capsules may be modified in an additional step of exposing the capsules to the surface modification additive, having said additive in the receiving bath makes the capsule production a 1-step process.

In conclusion, we demonstrated a novel template- and surfactant-free method for preparing polyelectrolyte complex capsules in one step by ultrasonic atomizing. Capsule size and wall thickness were controlled by several variables, including droplet size, polymer concentration and molecular weight, temperature, surface tension, and viscosity. Encapsulation of macromolecules and nanoparticles is conveniently accomplished by mixing these components into the PEC solution to be sprayed.

EXAMPLES

The following non-limiting examples are provided to further illustrate the present invention.

Materials and Methods

Materials:

Poly(4-styrenesulfonic acid, sodium salt) (AkzoNobel, VERSA TL130, molar mass ca. 200,000 g $mol^{-1}$) and poly(diallyldimethylammonium chloride) (Ondeo-Nalco, SD 46104, molar mass ca. 400,000 g $mol^{-1}$) were used as received. Rhodamine B isothiocyanate-Dextran (RBD) (Mw~70,000) was purchased from Sigma Aldrich. Superparamagnetic iron oxide nanoparticles (SPIONs) were prepared following our previous paper. See Z. G. Estephan, H. H. Hariri, J. B. Schlenoff, *Langmuir* 2013, 29, 2572. Tris (2,2'-bipyridyl)ruthenium(II) chloride hexahydrate (Rubpy)

was purchase from Fluka. All salt solutions were prepared using deionized water (18 MΩ Barnstead, E-pure).

PSS/PDADMA Complex:

PSSNa and PDADMAC solutions in 0.25M NaCl were prepared at a concentration of 0.125 M with respect to their monomer units and coprecipitated to yield PECs, dried and ground to powder as described previously. See R. F. Shamoun, A. Reisch, J. B. Schlenoff, *Adv. Funct. Mater.* 2012, 22, 1923. PECs in KBr solutions were typically prepared by dissolving the PEC powder in 2.50 M KBr with different weight percentages.

Methods and Equipment:

Typically, PEC solutions were pumped into an ultrasonic atomizer with a wide spray nozzle (Sonaer Inc.) with a syringe pump (model 352, SAGE Instruments) at 0.12 mL $min^{-1}$. The solution was atomized with an output of frequency of 45.5 KHz and power of 2.6 W. The atomized solution was sprayed into 200 mL 80±0.5° C. water in a 400 mL baker with magnetic stirring. PEC capsules or microstructures formed as KBr diffused out of the droplets in the reservoir. As-made capsules or microstructures were collected via sedimentation or centrifugation. For the loading of molecules or nanoparticles, a small volume of stock solution of RBD, SPION and quantum dots (QD) was added to the PEC solution and sprayed to make capsules.

Viscosities of solutions were measured with a temperature-controlled RheoStress 300 rheometer in a cone/plate configuration (C35/2Ti titanium plate with 2° cone and a diameter of 35 mm). Constant speed shear experiments were carried out with 1000 1/s for 60 s and the temperature set to 25.0±0.1° C. for PEC solutions with different KBr concentration. Surface tension of the PEC solutions was measured by Thermo Cahn DCA 315 dynamic content angle analyzer at 25.0±0.1° C. with a flamed glass slide.

For imaging, capsule samples were imaged with a Nikon Eclipse Ti inverted microscope fitted with a Photometrics Cool Snap HQ2 camera and NIS Elements AR 3.0 software. DIA and fluorescence images with different magnifications were obtained. The wall thicknesses of crushed capsules, at least 3 for each condition, were imaged by scanning electron microscopy (JEOL JSM-7401F). The surface morphology of the capsules was acquired with a MFP-3D AFM (Asylum Research Inc. Santa Barbara, Calif.) using the a.c. mode.

Example 1

Preparation of the Starting Polyelectrolyte Complex

Poly(4-styrenesulfonic acid, sodium salt) was from AkzoNobel (VERSA TL 130, MW of 200,000 g mol-1), and poly(diallyldimethylammonium chloride) from Ondeo-Nalco (SD 46104, with MW of 410,000 g mol-1). Sodium chloride (Aldrich) was used to adjust solution ionic strength. Deionized water (Barnstead, E-pure, Milli-Q) was used to prepare all solutions.

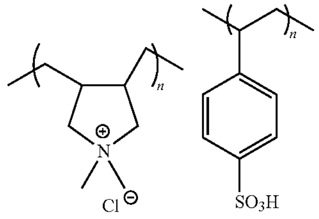

PDADMA PSS

Solutions of PSS and PDADMA were prepared at a concentration of 0.125M with respect to their monomer units, neutralized to pH 7 with NaOH and their ionic strength adjusted (usually to 0.25M NaCl). Typically, to prepare the starting polyelectrolyte complex, 1 L of each was poured simultaneously into a 3 L beaker. 1 L of 0.25 M NaCl, used to rinse the flasks, was added to the precipitate. The mixture was stirred with a magnetic stirrer for about 30 min and the precipitated PEC was decanted and washed with 1 L of 1M NaCl. The PEC was chopped into pieces between 5 mm and 10 mm large then soaked in 1.0 M NaCl for 24 hr. The salt solution was strained off and excess liquid removed from the PEC pieces by rapid dabbing with a paper towel.

To determine the salt content of the PECs, thermogravimetric analysis (TGA) was performed with a SDT Q600 TGA from TA Instruments. Prior to thermal analysis, samples were dried for 24 h at 90° C. in vac and gently ground.

Example 2

Stoichiometry of Starting Polyelectrolyte Complexes

Proton NMR spectroscopy (Bruker Avance 600 MHz spectrometer) was used to measure the ratio of PSS to PDADMAC in the PECs as follows: excess solution was removed from a piece of complex (50-100 mg) using paper wipes. To exchange most of the hydration $H_2O$ with $D_2O$ the complex was rinsed with 1M NaCl in $D_2O$ (in three 1 mL aliquots over 24 h). The piece of complex was then dissolved in 1 mL 2.5 M KBr in $D_2O$. For calibration, spectra of mixtures of known amounts of PSS and PDADMAC in 2.5 M KBr were recorded under the same conditions. Then the precipitates were redissolved in 2.5 M KBr in $D_2O$. In the solution 1H NMR spectra of these dissolved complexes, all the protons from the constituent polyelectrolytes were present. Integration of the signal of the four aromatic hydrogens of PSS (between 5.5 and 9 ppm) provided a convenient internal standard for comparison with the 16 aliphatic 1H (between 0 and 4.6 ppm) on PDADMA plus the three aliphatic 1H on PSS. The ratio PSS:PDADMA charged polyelectrolyte repeat units was 1:1, within an experimental error of +/−2%.

Example 3

Doping of PSS/PDADMA with Different Salts

Figure 1:
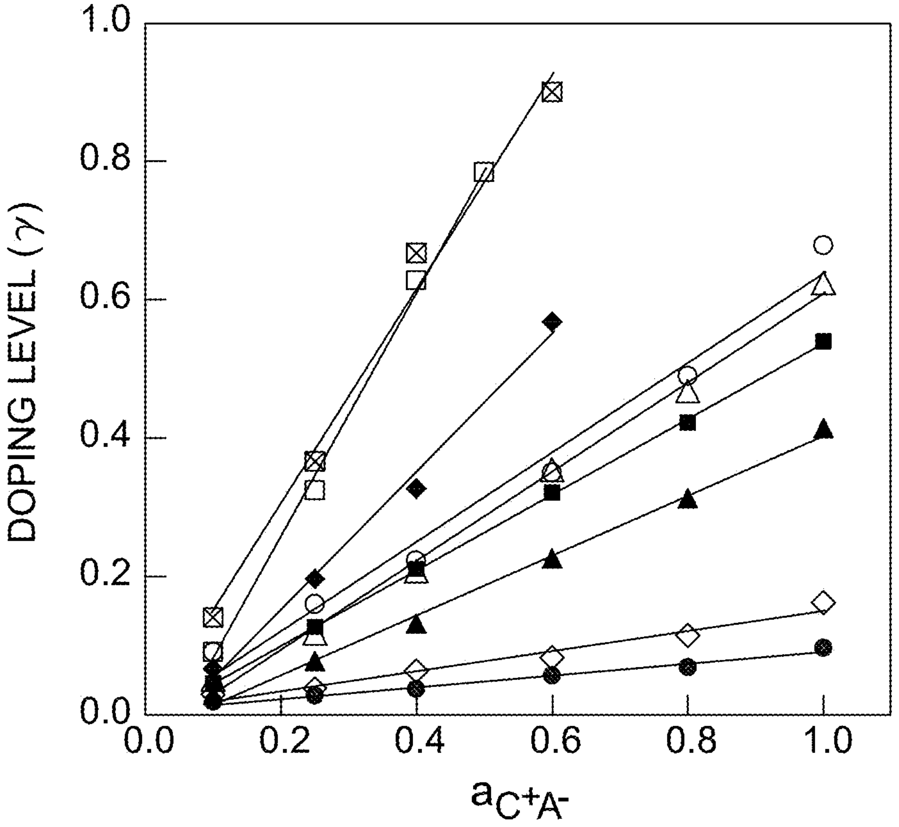
FIG. 1 is a graph depicting Doping level, γ, in PSS/PDADMA exPEC versus salt activity for NaF ($a_{C+A-}$). In the graph, the salts are as follows: (●); $NaCH_3COO$ (◇)

A conductivity meter, equipped with a water jacket and temperature controlled to 25±0.1° C., was standardized with NaCl solutions. After two consecutive extrusions, the stoichiometric (1:1 PSS:PDADMA) extruded polyelectrolyte complex, exPECs, from the Example above were annealed in 1.5 M NaCl for 24 h, then soaked in excess water to remove all ions. The exPEC rods were cut into samples approximately 1 cm long, dabbed dry with a paper wipe and immersed separately into solutions of various salts at different concentrations. Each sample was allowed to dope to equilibrium at room temperature (23±2° C.) for at least 24 h. PECs were wiped then dropped into 50 mL water in the conductivity cell equipped with a small stir bar. Conductivity values were recorded every 30 s for 90 min. After release of salt, exPECs were dried at 110° C. for 6 h to obtain the dry mass of the complex. All salt released was assumed to be doping the polymer. See FIG. 1 is a graph of Doping level, γ, in PSS/PDADMA exPEC versus salt activity for NaF. In the graph, the salts are as follows: (●); $NaCH_3COO$ (◇); $NaClO_3$ (▲); NaCl (■); $NaNO_3$ (Δ) NaBr (○); NaI (♦); $NaClO_4$ (x); and NaSCN (□). Room temperature. FIG. 1 shows doping level as a function of salt concentration in the doping solution.

This method is reliable for doping levels up to about 0.3 only. At doping levels higher than about 0.3 additional salt not paired with charged polyelectrolyte repeat units enters the complex. Hence, doping levels higher than 0.3 in FIG. 1 are only approximate.

Example 4

Doping at High Salt Concentration

A sample of starting polyelectrolyte complex of stoichiometric PDADMA/PSS was exposed to increasing concentrations of aqueous KBr solution and the molar ratio of KBr to polyelectrolyte in the complex was measured by conductivity, as described in the previous example. FIG. 2 is graph depicting Molar ratio of KBr to PSS/PDADMA polyelectrolyte complex in doped complex from 0.0M KBr to 1.90M KBr at room temperature. Transitions are shown by changing symbols from ♦ (complex) to ● (coacervate) to ■ (dissolved). At about 1.8M KBr (transition from ● to ■ in FIG. 2) the doping level reaches 1.00 and beyond this concentration of KBr the complex is dissolved and the polyelectrolyte molecules no longer associate with each other via ion pairing. Dotted line shows doping level, γ, as a function of KBr concentration. When [KBr] reaches about 1.8M the doping level reaches 1.00. FIG. 2 shows the ratio of moles KBr in the salt-doped complex to the moles of the dry PSS/PDADMA starting polyelectrolyte added.

Example 5

Viscosity of the Polyelectrolyte Complex Dope

The loss modulus, storage modulus, and viscosity of viscous polyelectrolyte complex dope in contact with aqueous KBr solutions was determined at room temperature using a parallel plate rheometer operating at a frequency of 0.1 Hz and a shear stress of 25 Pa. Three parameters are plotted in FIG. 3 as a function of KBr (salt) concentration: the storage modulus, G', the loss modulus, G" and the viscosity. FIG. 3 is a graph depicting dynamic modulus G' (○), G" (◇) and η (Δ) at frequency of 0.1 Hz, shear stress of 25 Pa. 1 centipoise, cP=1 milliPascal second, mPas. FIG. 3 clearly shows how all parameters decrease dramatically with the addition of salt. The storage modulus represents an elastic component of the viscoelastic response of the polyelectrolyte complex dope. It is seen that the storage modulus falls to unmeasureable values with sufficient salt. At a concentration of 1.8M KBr there is a sudden change in the slope of viscosity vs. [KBr] at the point where the doping level reaches 1.00 and the polyelectrolytes are dissolved (i.e. separated). At any point below 1.8M KBr the doping level is less than 1.00. The viscosity range in FIG. 3 suitable for the present invention is from about 100 to about 10E4 cP.

Example 6

Spraying the Dope

The starting polyelectrolyte PDADMA/PSS complex was dissolved in 2.5M KBr to make a polyelectrolyte complex dope from 1% by weight to 8% by weight polymer. Typically, PEC solutions were pumped into an ultrasonic atomizer with a wide spray nozzle (Sonaer Inc.,) with a syringe pump (model 352, SAGE Instruments) at 0.12 mL min-1. The solution was atomized with an output of frequency of 45.5 KHz and power of 2.6 W. The atomized solution was sprayed into 200 mL 80±0.5° C. water in a 400 mL baker with magnetic stirring. PEC capsules or microstructures formed as KBr diffused out of the droplets in the water bath. As-made capsules or microstructrues were collected via sedimentation or centrifugation. For imaging, capsule samples were sealed between a cover slip and a microscope slide and imaged with a Nikon Eclipse Ti inverted microscope fitted with a Photometrics Cool Snap HQ2 camera and NIS Elements AR 3.0 software. DIA and fluorescence images with different magnifications were obtained. The wall thickness of the crushed capsules were imaged by scanning electron microscopy (SEM, JEOL JSM-7401F). The surface morphology of the capsules was acquired with a MFP-3D AFM (Asylum Research Inc. Santa Barbara, Calif.) using the intermittent contact mode. To accelerate the diffusion of KBr out of the droplets the water reservoir was maintained at 80° C. This temperature also keeps the PEC elastic and prevents it from bursting under the osmotic pressure.

FIG. 4A depicts average diameters (□) and relaxation ratios r (○) vs. the PEC wt. % (a). FIG. 4B depicts size distribution of capsules prepared with 2% by weight PEC (■), 3% by weight PEC (○), 4% by weight PEC (▲), 6% by weight PEC (▼) and 8% by weight PEC (◇). The curves show the Gaussian fitting. FIGS. 4C, 4D, 4E, 4F, and 4G are SEM images of PEC capsules prepared according to the method of the present invention. The capsules are prepared with 2% by weight PEC (FIG. 4C), 3% by weight PEC (FIG. 4D), 4% by weight PEC (FIG. 4E), 6% by weight PEC (FIG. 4F) and 8% by weight PEC (FIG. 4G). FIGS. 4C through 4G depict the capsules as-prepared and as partially-crushed. FIGS. 4H, 4I, 4J, 4K, and 4L microscopic images of PEC capsules prepared with 2% by weight PEC (FIG. 4H), 3% by weight PEC (FIG. 4I), 4% by weight PEC (FIG. 4J), 6% by weight PEC (FIG. 4K) and 8% by weight PEC (FIG. 4L). The scale bars are 10 μm (white) and 100 μm (black).

As-prepared PEC capsules are shown in FIGS. 4C through 4G. The morphology is highly sensitive to the PEC concentration. With 1% by weight PEC, broken pieces instead of capsules were observed. At the other concentration extreme, 8% by weight PEC yielded irregular spheroids (potato shaped) containing multiple large pores. For PEC concentration between 2% by weight and 8% by weight, capsules were formed with wall thickness increasing with PEC %.

FIG. 5A is an SEM image of a broken PEC capsule. This sample was prepared with 4% by weight PEC solution. FIG. 5B is an AFM image of a surface of a PEC capsule. This sample was prepared with 4% by weight PEC solution. The SEM image shows the cross section and inside of the wall is dense and smooth. See FIG. 5A. The AFM image of the surface morphology shows there are small dimples on the outer surface of the droplet. See FIG. 5B. Considering the successful encapsulation of polymers, it is safe to say the holes do not run through the wall.

Example 7

Encapsulating Materials

Dextran, a neutral polymer (molecular weight ca 70,000) tagged with Rhodamine B (RBD) and superparamagnetic iron oxide nanoparticles (SPIONs) with size about 12 nm were tested as models for loading in the capsules. RBD and SPIONs were mixed with 4 wt. % PEC at a concentration of 1 and 2 mg g-1, respectively, and these mixtures were sprayed under the same conditions as for pure PEC solution.

FIGS. 6A, 6B, and 6C are microscopy and fluorescence microscopy images of PEC microcapsules loaded with RB-D (FIG. 6A), Rubpy (FIG. 6B) and SPION (FIG. 6C). FIG. 6D is a photo of PEC microcapsules controlled by magnetic field. The scale bars are 10 (white) and 100 (black) μm.

The resulting capsules are shown in FIG. 6A. Fluorescence microscopy of RBD encapsulated PEC capsules clearly shows the concentrated red fluorescence of RBD at the center and blue fluorescence of PSS in PEC wall. SPIONs encapsulated PEC capsules also show the same morphology as PEC capsules. See FIG. 6C and FIG. 6D. The photo of magnetic field manipulation of SPION encapsulated PEC capsules is shown, too.

To address whether small molecules could be encapsulated, tris(2,2'-bipyridyl)ruthenium(II) chloride (Rubpy) was mixed with 4% by weight PEC solution at a concentration of 1 mg g-1 and capsules were prepared with the mixture solution. No strong fluorescence of Rubpy was observed inside the capsules, which means all Rubpy diffused out during or after formation. See FIG. 6B. For those materials not suitable for relatively high temperatures, postloading by altering the permeability of the capsule and entrapping them into the capsules is also possible.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A method of forming a capsule, the method comprising:

spraying a polyelectrolyte solution comprising a dissolved positively charged polyelectrolyte and a dissolved negatively charged polyelectrolyte into a liquid receiving bath, wherein upon impacting the liquid receiving bath, the positively charged polyelectrolyte and a negatively charged polyelectrolyte coalesce into a capsule comprising a wall, and further wherein the wall of the capsule comprises an interpenetrating complex of the positively charged polyelectrolyte and the negatively polyelectrolyte.

2. The method of claim 1 wherein the dissolved positively charged polyelectrolyte and the dissolved negatively charged polyelectrolyte are dissolved in the polyelectrolyte solution comprising a solvent selected from the group consisting of water, acetone, ethanol, methanol, trifluoroethanol, and any combination thereof.

3. The method of claim 1 wherein the polyelectrolyte solution comprises the dissolved positively charged polyelectrolyte at a concentration between about 1% by weight and about 10% by weight and further comprises the dissolved negatively charged polyelectrolyte at a concentration between about 1% by weight and about 10% by weight.

4. The method of claim 1 wherein the polyelectrolyte solution comprises the dissolved positively charged polyelectrolyte at a concentration between about 1% by weight and about 5% by weight and further comprises the dissolved negatively charged polyelectrolyte at a concentration between about 1% by weight and about 5% by weight.

5. The method of claim 1 wherein the polyelectrolyte solution comprises the dissolved positively charged polyelectrolyte at a concentration between about 5% by weight and about 10% by weight and further comprises the dissolved negatively charged polyelectrolyte at a concentration between about 5% by weight and about 10% by weight.

6. The method of claim 1 wherein the polyelectrolyte solution further comprises at least one dissolved salt.

7. The method of claim 1 wherein the polyelectrolyte solution further comprises two or more dissolved salts.

8. The method of claim 1 wherein the polyelectrolyte solution further comprises at least one dissolved salt and further wherein the dissolved salt concentration in the polyelectrolyte solution is between about 0.1M and about 5M.

9. The method of claim 1 wherein the liquid receiving bath comprises a liquid selected from the group consisting of water, an organic solvent, and a combination thereof.

10. The method of claim 1 wherein the liquid receiving bath further comprises dissolved salt.

11. The method of claim 10 wherein the dissolved salt concentration in the liquid receiving bath is between about 0.01M and about 1M.

12. The method of claim 1 wherein the liquid receiving bath further comprises a polymer comprising ethylene glycol repeat units.

13. The method of claim 1 wherein the liquid receiving bath further comprises a polymer comprising zwitterionic repeat units.

14. The method of claim 1 wherein the polyelectrolyte solution has a viscosity of between about 1 poise and about 1000 poise, at room temperature.

15. The method of claim 1 wherein the wall of the capsule has thickness between about 0.1 micrometers and about 100 micrometers.

16. The method of claim 1 wherein the capsule is spherical, and further wherein the diameter of the spherical capsule is between about 0.1 micrometers and about 100 micrometers.

17. The method of claim 1 wherein the capsule is spherical, and further wherein a ratio of the diameter of the spherical capsule to the thickness of the wall of the capsule is between 100 and 0.1.

18. The method of claim 1 wherein the polyelectrolyte solution further comprises a pharmaceutically active compound.

19. The method of claim 1 wherein the spray is produced by ultrasonic atomization.

20. The method of claim 1 wherein the liquid receiving bath is maintained at a temperature between about 30° C. and about 90° C.

21. A method of forming a capsule, the method comprising:

spraying a coacervate comprising a positively charged polyelectrolyte and a negatively charged polyelectrolyte into a liquid receiving bath, wherein upon impacting the liquid receiving bath, the positively charged polyelectrolyte and a negatively charged polyelectrolyte coalesce into a capsule comprising a wall, and further wherein the capsule wall comprises an interpenetrating complex of the positively charged polyelectrolyte and the negatively polyelectrolyte.

22. The method of claim 21 wherein the coacervate further comprises at least one salt.

23. The method of claim 21 wherein the coacervate further comprises two or more salts.

24. The method of claim 21 wherein the coacervate further comprises at least one salt and further wherein the salt concentration in the polyelectrolyte solution is between about 0.1M and about 5M.

25. The method of claim 21 wherein the liquid receiving bath comprises a liquid selected from the group consisting of water, an organic solvent, and a combination thereof.

26. The method of claim 21 wherein the liquid receiving bath further comprises dissolved salt.

27. The method of claim 26 wherein the dissolved salt concentration in the liquid receiving bath is between about 0.01M and about 1M.

28. The method of claim 21 wherein the liquid receiving bath further comprises a polymer comprising ethylene glycol repeat units.

29. The method of claim 21 wherein the liquid receiving bath further comprises a polymer comprising zwitterionic repeat units.

30. The method of claim 21 wherein the wall of the capsule has thickness between about 0.1 micrometers and about 100 micrometers.

31. The method of claim 21 wherein the capsule is spherical, and further wherein the diameter of the spherical capsule is between about 0.1 micrometers and about 100 micrometers.

32. The method of claim 21 wherein the capsule is spherical, and further wherein a ratio of the diameter of the spherical capsule to the thickness of the wall of the capsule is between 100 and 0.1.

33. The method of claim 21 wherein the polyelectrolyte solution further comprises a pharmaceutically active compound.

34. The method of claim 21 wherein the spray is produced by ultrasonic atomization.

35. The method of claim 21 wherein the liquid receiving bath is maintained at a temperature between about 30° C. and about 90° C.

* * * * *